United States Patent
Littlefield et al.

(10) Patent No.: US 7,142,701 B2
(45) Date of Patent: Nov. 28, 2006

(54) CRANIAL REMODELING DEVICE MANUFACTURING SYSTEM

(75) Inventors: Timothy R Littlefield, Goodyear, AZ (US); Jeanne K Pomatto, Scottsdale, AZ (US)

(73) Assignee: Cranial Technologies, Inc., Tempe, AZ (US)

( * ) Notice: Subject to any disclaimer, the term of this patent is extended or adjusted under 35 U.S.C. 154(b) by 491 days.

(21) Appl. No.: 10/752,800

(22) Filed: Jan. 7, 2004

(65) Prior Publication Data

US 2004/0197016 A1 Oct. 7, 2004

Related U.S. Application Data

(63) Continuation-in-part of application No. 10/385,307, filed on Mar. 10, 2003.

(51) Int. Cl.
*G06K 9/00* (2006.01)
*A61F 5/00* (2006.01)

(52) U.S. Cl. .......................................... 382/128; 602/17

(58) Field of Classification Search ................ 382/128, 382/154; 128/922; 345/419–420; 600/587; 602/17–18; 700/118

See application file for complete search history.

(56) References Cited

U.S. PATENT DOCUMENTS

| | | | | |
|---|---|---|---|---|
| 5,094,229 | A | * | 3/1992 | Pomatto et al. ............... 602/17 |
| 5,951,503 | A | * | 9/1999 | Pomatto ....................... 602/17 |
| 6,340,353 | B1 | * | 1/2002 | Pomatto et al. ............... 602/17 |
| 6,423,019 | B1 | * | 7/2002 | Papay et al. .................. 602/17 |
| 6,536,058 | B1 | * | 3/2003 | Chang ............................ 5/636 |
| 6,572,572 | B1 | * | 6/2003 | Pomatto et al. ............... 602/17 |
| 6,957,961 | B1 | * | 10/2005 | Owens et al. ................ 434/270 |

* cited by examiner

*Primary Examiner*—Daniel Mariam
(74) *Attorney, Agent, or Firm*—Donald J. Lenkszus

(57) ABSTRACT

A system is described that captures accurate three-dimensional images of infant heads without the infant being absolutely stationary or fixed in one particular orientation and which automatically produces a cranial remodeling device customized for that particular infant's head to provide appropriate cranial remodeling correction.

46 Claims, 21 Drawing Sheets

| | |
|---|---|
| 1001 | PRODUCE CAST OF FIRST SHAPE |
| 1003 | PRODUCE CAST OF SECOND CORRESPONDING SHAPE |
| 1005 | DIGITALLY CAPTURE FIRST SHAPE |
| 1007 | PRODUCE FIRST DIGITAL DATA |
| 1009 | STORE FIRST DIGITAL DATA IN DATABASE |
| 1011 | DIGITALLY CAPTURE CORRESPONDING SECOND SHAPE |
| 1013 | PRODUCE SECOND DIGITAL DATA |
| 1015 | STORE SAID SECOND DIGITAL DATA IN SAID DATABASE |
| 1017 | PROVIDE ONE TO ONE CORRESPONDENCE BETWEEN EACH FIRST DIGITAL DATA AND CORRESPONDING SECOND DIGITAL DATA |

FIG. 10

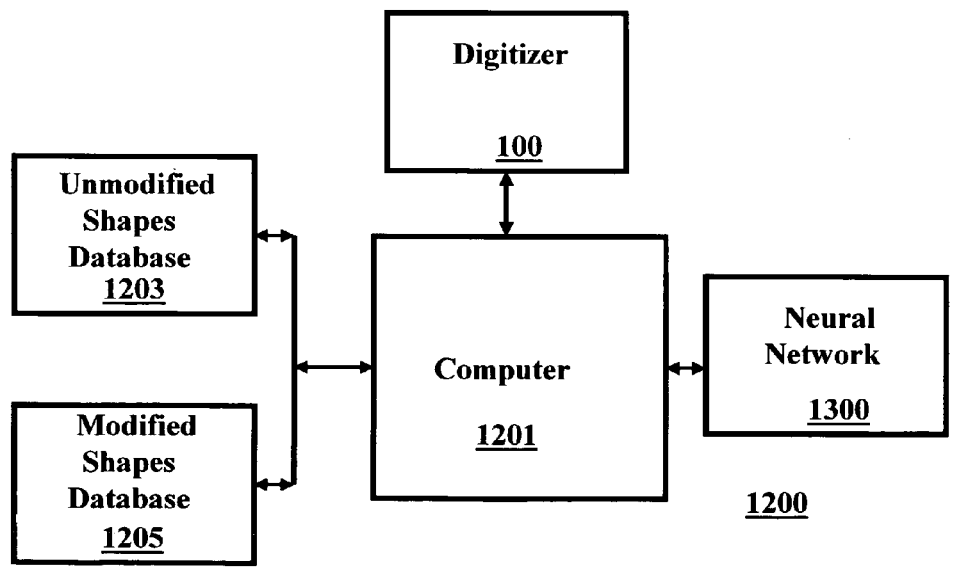

FIG. 11

1401 PROVIDING A DATABASE OF FIRST OR UNMODIFIED SHAPES

1403 PROVIDING A DATABASE OF CORRESPONDING SECOND OR MODIFIED SHAPES

1405 ALIGNING EACH OF SAID FIRST OR UNMODIFIED SHAPES TO THE SAME ORIENTATION

1407 ALIGNING EACH SECOND OR MODIFIED SHAPES AND THE CORRESPONDING FIRST OR UNMODIFIED SHAPE

1409 NORMALIZE DATA

1411 UTILIZING PRINCIPAL COMPONENT ANALYSIS WITH ALIGNED FIRST OR UNMODIFIED SHAPES AND CORRESPONDING ALIGNED SECOND OR MODIFIED SHAPES TO DETERMINE PCA COEFFICIENTS

1413 PROVIDING OR MORE NEURAL NETWORK

1415 TRAINING NEURAL NETWORK WITH A LEAST SQUARES SUPPORT VECTOR MACHINE

1417 UTILIZING TRAINED NEURAL NETWORK TO OPERATE ON A NEW UNMODIFIED SHAPE TO PRODUCE A CORRESPONDING MODIFIED SHAPE

FIG. 13

| Hyperparameter | | |
|---|---|---|
| PCA Coefficient | Gamma | Sigma |
| 1 | 20 | 33 |
| 2 | 32 | 77 |
| 3 | 17 | 107 |
| 4 | 68 | 86 |
| 5 | 47 | 47 |
| 6 | 32 | 122 |
| 7 | 62 | 62 |
| 8 | 92 | 92 |
| 9 | 56 | 134 |
| 10 | 77 | 77 |
| 11 | 62 | 50 |
| 12 | 92 | 92 |
| 13 | 62 | 92 |
| 14 | 77 | 152 |
| 15 | 77 | 77 |
| 16 | 107 | 62 |
| 17 | 77 | 62 |
| 18 | 137 | 32 |
| 19 | 77 | 62 |
| 20 | 68 | 47 |
| 21 | 92 | 62 |
| 22 | 107 | 77 |
| 23 | 173 | 83 |
| 24 | 122 | 62 |
| 25 | 122 | 122 |
| 26 | 62 | 107 |
| 27 | 62 | 92 |
| 28 | 122 | 68 |
| 29 | 182 | 116 |
| 30 | 182 | 128 |
| 31 | 92 | 38 |
| 32 | 182 | 92 |
| 33 | 182 | 92 |
| 34 | 152 | 152 |
| 35 | 182 | 92 |
| 36 | 182 | 122 |
| 37 | 128 | 122 |
| 38 | 152 | 152 |
| 39 – 64 | 160 | 125 |

FIG. 14

CRANIAL REMODELING DEVICE MANUFACTURING SYSTEM

RELATED APPLICATIONS

This application is a continuation-in-part of copending U.S. application Ser. No. 10/385,307 filed Mar. 10, 2003, for Three-Dimensional Triage Capture System by T. Littlefield and J. Pomatto and assigned to a common assignee. The following related patent applications are being filed on even date herewith and are assigned to a common assignee: Ser. No. 10/753,012, Method And Apparatus For Producing Three Dimensional Shapes by T. Littleflold, J. Pomatto and G. Kechter: Ser. No. 10/753,013, Cranial Remodeling Device Database by T. Littlefield and J. Pomatto: Ser. No. 10/753,118, Automatic Selection of Cranial Remodeling Device Configuration T. Littlefield and J. Pomatto: Ser. No. 10/753,118, Automatic Selection of Cranial Remodeling Device Configuration by T. Littlefleld and J. Pomatto. The disclosures of all the above-identified applications are incorporated herein.

FIELD OF THE INVENTION

This invention pertains to a system and method for producing cranial remodeling devices.

BACKGROUND OF THE INVENTION

Cranial remodeling is utilized to correct for deformities in the head shapes of infants. Prior to the development of the Dynamic Orthotic Cranioplasty$^{SM}$ method of cranial remodeling by Cranial Technologies, Inc, the assignee of the present invention, the only viable approach for correction of cranial deformities was surgical correction of the shape of the cranium. Dynamic Orthotic Cranioplasty$^{SM}$ utilizes a treatment program in which a cranial remodeling band is custom produced for each infant to be treated. The band has an internal shape that produces the desired shape of the infant's cranium.

In the past, a cranial remodeling device or band was produced by first obtaining a full size and accurate model of the infants actual head shape. This first model or shape was then modified to produce a second or desired head shape. The second or desired head shape is used to form the cranial remodeling band for the infant. The first shape was originally produced as a cast of the infant's head. The second shape was similarly produced as a cast of the head and manually modified to form the desired shape.

Various arrangements have been considered in the past to automate the process of producing cranial remodeling devices. In some of the prior arrangements a scanner is utilized to obtain three dimensional data of an infant's head. Such arrangements have the disadvantage in that scanners cannot obtain instantaneous capture of data of the entirety of an infant's head. In addition, it has been proposed to utilize expert systems to operate on scanned data to produce an image of a modified head shape from which a cranial remodeling device may be fabricated. However, because each head shape is unique, even the use of an expert system may not present an optimized solution to developing modified shapes suitable for producing a cranial remodeling device.

Various systems are known for the capturing of images of objects including live objects. One category of such systems typically utilizes a scanning technology with lasers or other beam emitting sources. The difficulty with systems of this type is that to scan a three-dimensional object, the scan times limit use of the systems to stationary objects.

A second category of image captures systems utilizes triangulated cameras with or without projection of structured light patterns on the object. However, these systems typically are arranged to capture a three-dimensional image of only a portion of the object. Typically such systems also are used only with stationary objects.

It is highly desirable to provide an image capturing system that will capture three-dimensional images of objects that are not stationary, but which may move. It is also desirable that the three-dimensional image has high resolution and high accuracy. It is particularly desirable that the three-dimensional image captures the totality of the object.

It is particularly desirable to provide an image capturing system that will have the ability to capture an accurate three-dimensional image of an infant's head. Capturing of such an image has not been possible with prior image capturing systems for a variety of reasons, one of which being that infants are not stationary for the times that prior systems require to scan or capture the data necessary to produce a three-dimensional image. Another reason is that prior systems could only acquire a partial three-dimensional imager portion. The need for such a system is for producing cranial remodeling bands is great.

Prior to the present invention, the process by which a cranial remodeling band is fabricated required obtaining a negative or 'cast' impression of the child's head. The cast is obtained by first pulling a cotton stockinet over the child's head, and then casting the head with quick setting, low temperature plaster.

The casting technique takes approximately 7 to 10 minutes. After the initial casting, a plaster model or cast of the infant's head is made and is used for the fabrication of the cranial remodeling band.

It is highly desirable to simplify the process by utilizing digitization techniques to produce useful digital three-dimensional images of the entire head. We undertook an exhaustive search to identify and evaluate different digitization techniques. Numerous laser scanning, structured light, Moire, and triangulated CCD camera systems were evaluated and rejected as inadequate for one reason or another.

Prior digitization techniques and systems fail to recognize the particular unique challenges and requirements necessary for a system for the production of digital images of infant heads. The infant patients range in age from three to eighteen months of age. The younger infants are not able to follow verbal instructions and are not able to demonstrate head control while the older infants are difficult to control for more than a brief moment of time. A wide variety of head configurations, skin tone, and hair configurations also needed to be captured. A digitization system must acquire the image in a fraction of a second, i.e., substantially instantaneously, so that the child would not need to be restrained during image capture, and so that movement during image acquisition would not affect the data. The system data capture must be repeatable, accurate and safe for regular repeated use. In addition, to be used in a clinical setting the system must be robust, easy to use, and easy to calibrate and maintain without the need for hiring additional technical staff to run the equipment. Image acquisition, processing, and viewing of the data must be performed in substantially real time in order to ensure that no data was missing before allowing the patient to leave the office.

Numerous existing digitization techniques were evaluated. Laser scanning methods have the disadvantage of the long time, typically 14–20 seconds, that is required to scan an object. Because of the long time, an infant being scanned would have to be restrained in a specific orientation for the scan time. Recent advances in laser scanning have produced scan systems that can perform a scan in 1–2 seconds. However even this scan rate is too slow for an unrestrained infant. The use of lasers also raises concerns regarding their appropriateness and safety for use with an infant population. While many prior digitization systems use 'eye safe' lasers, the use of protective goggles is still frequently recommended.

Structured-light Moire and phase-shifted Moire systems used in certain 3D imaging systems are difficult to calibrate, are costly, and are relatively slow and therefore are not suitable for use in obtaining images of infants. In addition these systems are incapable of capturing the entirety of an object in one time instant.

Computed Tomography (CT) and Magnetic Resonance Imaging (MRI) are not particularly useful for the present application simply due to size, expense and concerns regarding radiation and the need to anesthetize the infant.

Prior systems that rely solely on triangulation of digital cameras proved to have insufficient accuracies, particularly as the object being imaged varied in shape and size from a calibration standard.

Structured light systems that combined triangulated digital cameras with a projected grid or line pattern can capture only one surface at a time because the grids projected by multiple projectors interfered with each other resulting in a loss of data. In addition, the images captured by this structured light systems need to be fit together like a three-dimensional jigsaw puzzle, and required that markers be placed on the subject in order to facilitate this registration process.

SUMMARY OF THE INVENTION

We have developed a system that captures accurate three-dimensional images of infant heads without the infant being absolutely stationary or fixed in one particular orientation, provides digital data representative of the infant's head and which produces a cranial remodeling device customized for that particular infant's head to provide appropriate cranial remodeling correction.

BRIEF DESCRIPTION OF THE DRAWING

The invention will be better understood from a reading of the following detailed description of embodiments of the invention taken in conjunction with the drawing figures in which like reference designators are used to identify like elements, and in which:

FIG. 10 illustrates steps in a method in accordance with the principles of the invention;

FIG. 11 is a block diagram of a system in accordance with the principles of the invention;

FIG. 13 illustrates steps in accordance with another aspect of the invention;

FIG. 14 is table;

DETAILED DESCRIPTION

Figure 1:
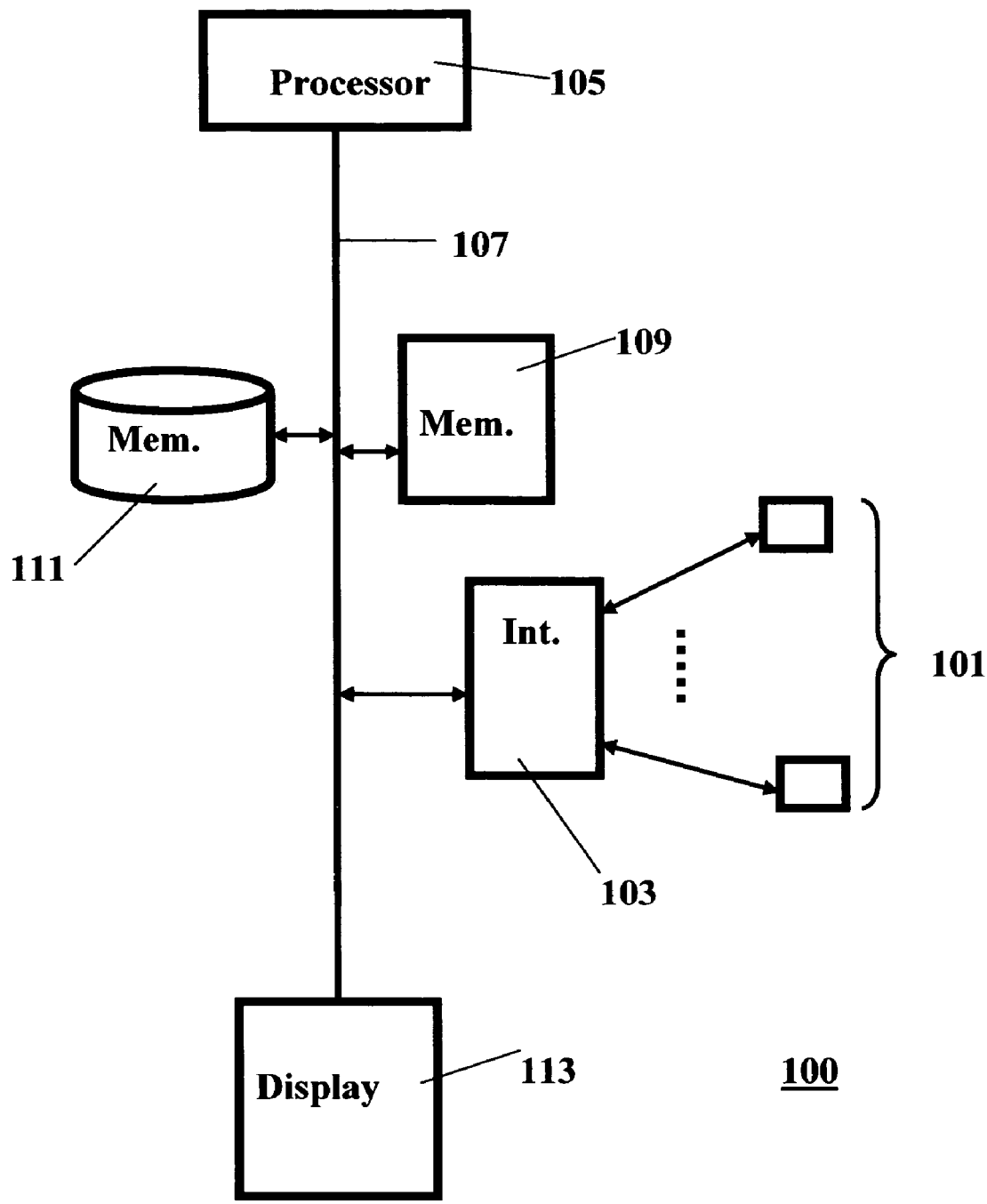
FIG. 1 is a block diagram of an image capture system in accordance with the invention.

Turning now to FIG. 1, a block diagram of an image capture system or digitizer 100 is shown in block diagram form. System 100 includes a plurality of image capturing apparatus 101. Each image capturing apparatus is operable such that a three-dimensional image is captured for a surface portion of an object that is disposed within the field of view of the image capturing apparatus.

The image capturing apparatus 101 are all coupled to and controlled by processing apparatus 105 via a bus 107. In addition processing apparatus 105 has associated with it program memory 109 and data memory 111. It will be understood by those skilled in the art that processing apparatus 105 may include one or more processors that are commercially available from a wide variety of sources, such as the Intel Pentium 4 or Itanium chip based processors. Program memory 109 and data memory 111 may be the same memory, or each may comprise a plurality of memory units.

Program memory 109 includes an image-processing algorithm that is utilized to process digitized three-dimensional images of surface portions provided by image capturing apparatus 101 to produce a digitized image of the entirety of an object.

In operation, processor apparatus 105 controls image capture apparatus 101 such that all of image capture apparatus 101 are simultaneously operated to capture digitized first images of corresponding surface portions of an object.

The digitized first images are uploaded into data memory 111 under control of processor apparatus 105.

Processor apparatus 105 operates on the digitized first images stored in memory 111 in accordance with the first algorithm stored in memory 109 to produce a composite three-dimensional digitized image from all of the first digitized images. The composite three-dimensional digital image is stored in memory 111 by processor 105. A display 113 coupled to processor apparatus 105 may be used to display the three-dimensional composite image of the object.

Figure 2:
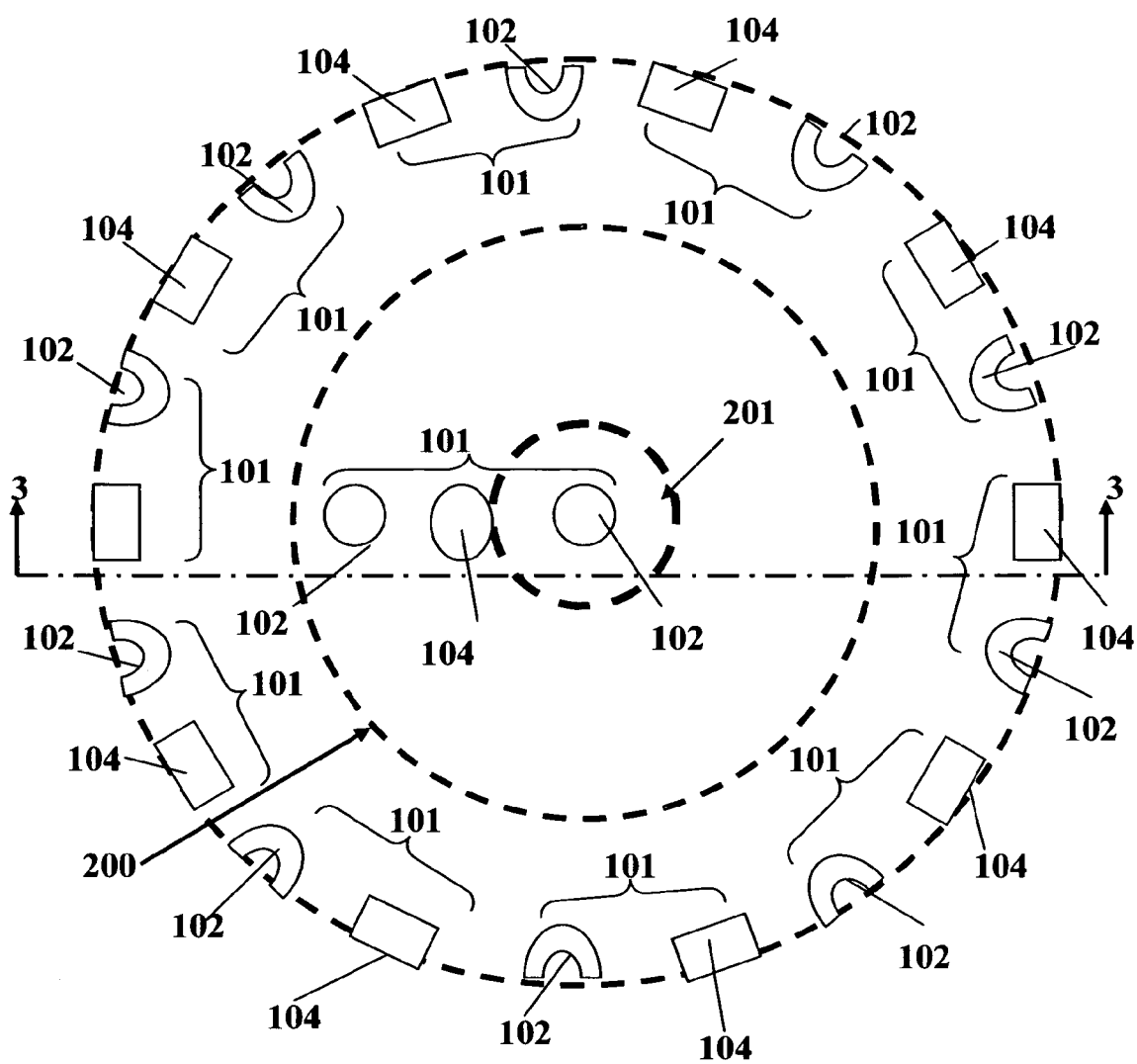
FIG. 2 is a top view of a portion of the image capture system of FIG. 1.
Figure 3:
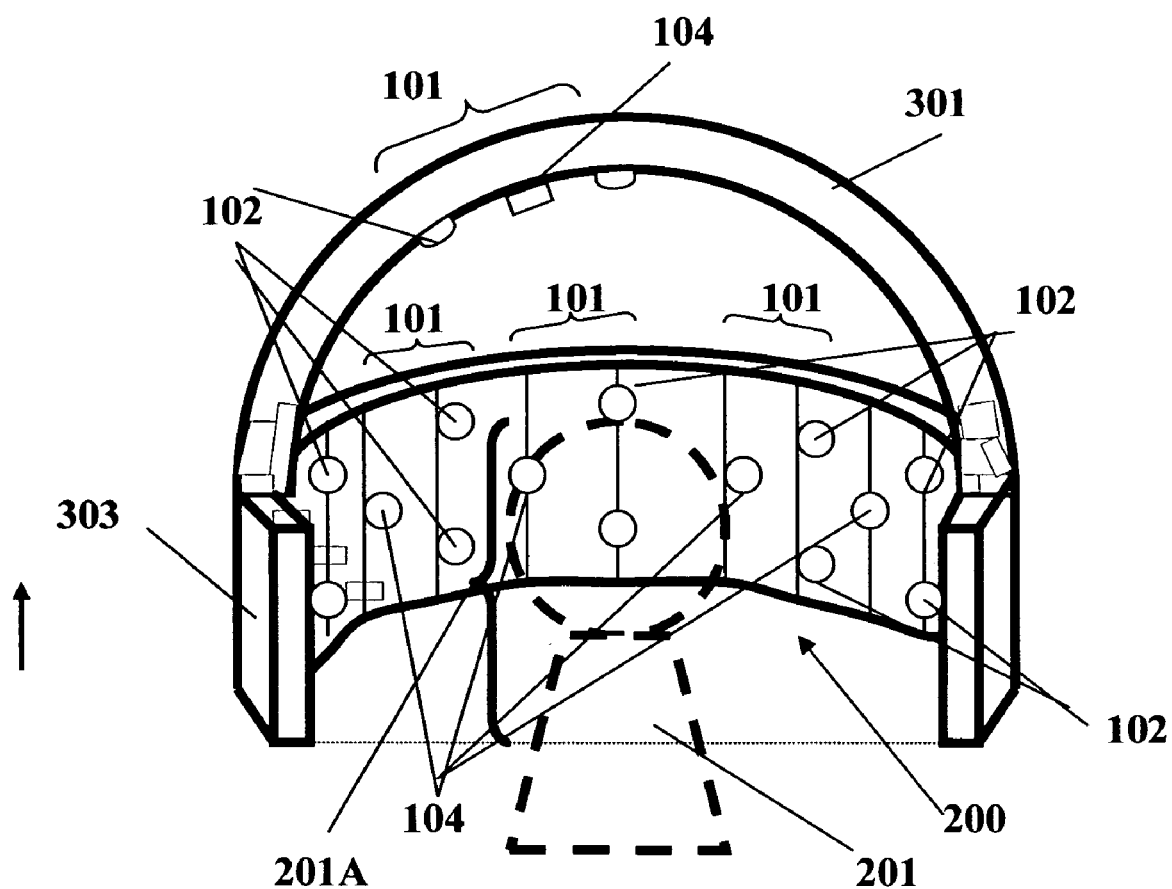
FIG. 3 is a cross-section take along lines 3—3 of the image capture system portion of FIG. 2.

The plurality of image capturing apparatus 101 are arranged to define a space 200 within which a three-dimensional image is captured of an object 201. As shown in FIGS. 2 and 3 the image capturing apparatus 101 are arranged to define a space 200 in the shape of a hemisphere. Although the illustrative embodiment defines a hemispherical shape, it will be understood by those skilled in the art that the defined space may be of a different configuration. It should also be apparent to those skilled in the art that the principles of the invention are not limited to the positioning of image capturing apparatus to any particular shape object 201. For certain objects 201, the image capturing apparatus may define a full sphere. In other implementations, the image capturing apparatus may define a space that is elongated in one or more directions. It will also be apparent to those skilled in the art that the size of the space 200 will be determined by the characteristics of the plurality of image capturing apparatus.

The number and positioning of image capturing apparatus 101 are selected to achieve a predetermined accuracy and resolution. The image capture speed of the image capturing apparatus 101 is selected to provide a "stop-action" image of the object 201. Thus, for example, conventional photographic speeds may be used to determine the top speed of an object 201 that moves within the space 200. To the extent that an object 201 extends outside of space 200, that portion 201A of object 201 that is within space 200 will be image captured such that the entirety of that portion 201A that is within space 200 will captured as a digitized three-dimensional image.

Figure 4:
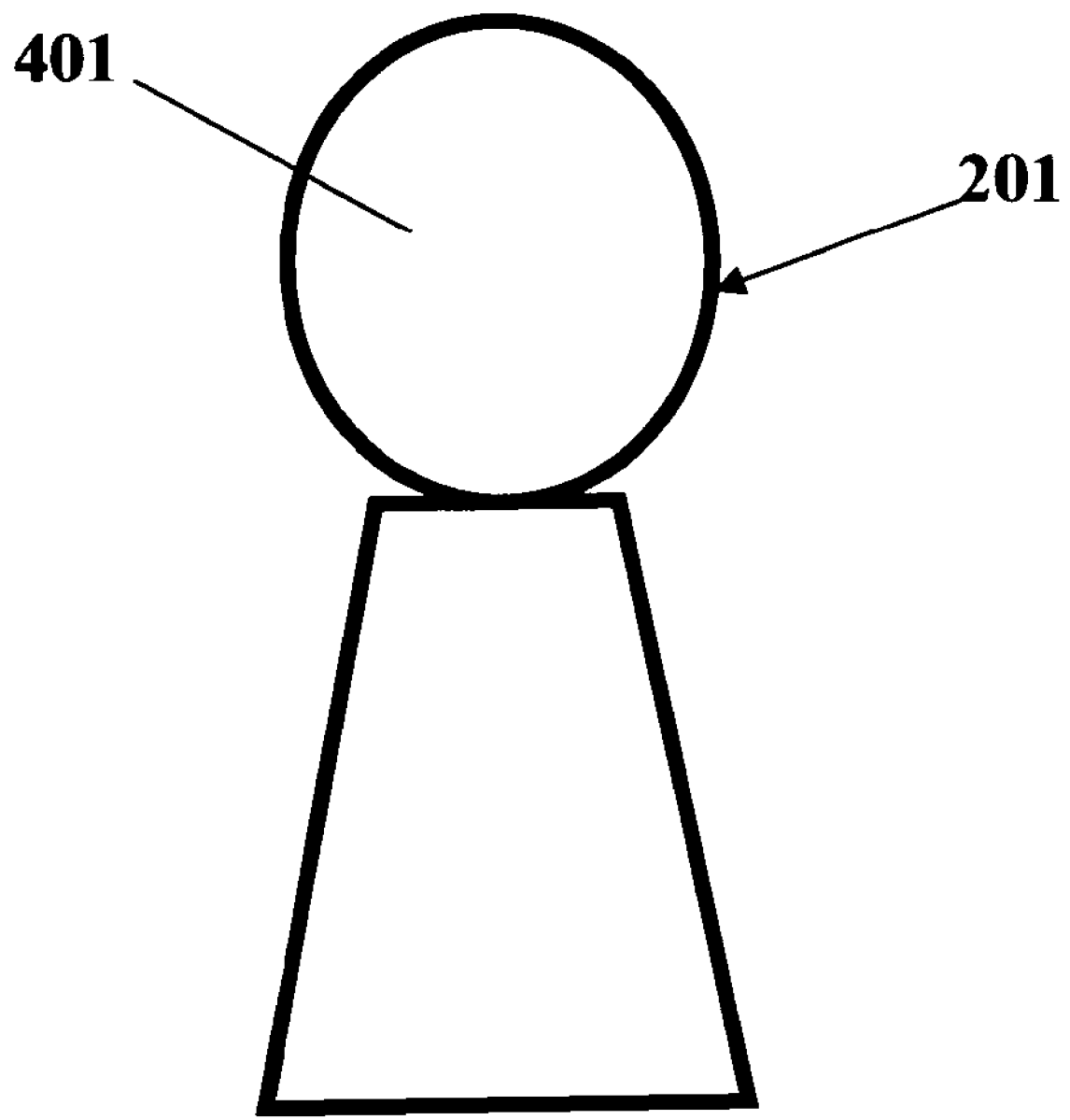
FIG. 4 is a representation of a random infrared image projected onto an object for which an image is to be captured.

In the illustrative embodiment of the invention, each image capturing apparatus 101 includes a plurality of digital cameras 102 such as CCD (charge coupled device) cameras 102 and a projector 104. Each CCD camera 102 is a high-resolution type camera of a type that is commercially available. Each projector 104 projects a pattern onto the object to facilitate processing of the images captured by the plurality of digital cameras 102 within an image capturing apparatus 101 into a three-dimensional image of a corresponding portion of the object 201. Projector 104 projects a random infrared pattern 401 as shown in FIG. 4 onto the object 201 that permits an algorithm to easily utilize triangulation to generate a digitized three-dimensional representation of the corresponding portion of object 201.

The CCD cameras 102 and projectors 104 may be supported on one or more supports such as the representative supports or support members 301, 303 shown in FIG. 3.

A particularly useful application of digitizer 100 is for use in capturing three-dimensional images of the totality of an infant's head. Producing a three-dimensional image of an infant is particularly difficult because infants do not remain motionless. Furthermore the motion that an infant may make is somewhat unpredictable. The infant may move his or her head in one direction while tilting and rotating it. The motion may be smooth or it may be jerky. The infant may move his head in one direction while rotating it in the opposite direction. It therefore is important that the system operate at a speed to capture the entirety of the infant's head in one instant. To provide a digitizer which utilizes a safe and noninvasive method of obtaining a 3D model of an infant's cranium, technological challenges had to be overcome that were not immediately evident during the initial stages of development. To be useful in a clinical setting, a digitizer must be fast, safe, accurate, repeatable, quiet, capture all skin tones, be impervious to motion, and not require the child to be restrained in a specific orientation. To be useful, the digitizer captures a 360° image which includes the face, top of the head, and lower occiput/neck region. A photographic image of the child is acquired and can be seamlessly overlaid on the three-dimensional display of the head to guarantee patient identification. The digitized model is processed and visualized within minutes to ensure that no data are missing before allowing the patient to leave the office. Calibration and operation of digitizer 100 is simple, fast, and robust enough to handle normal clinical operation.

Figure 5:
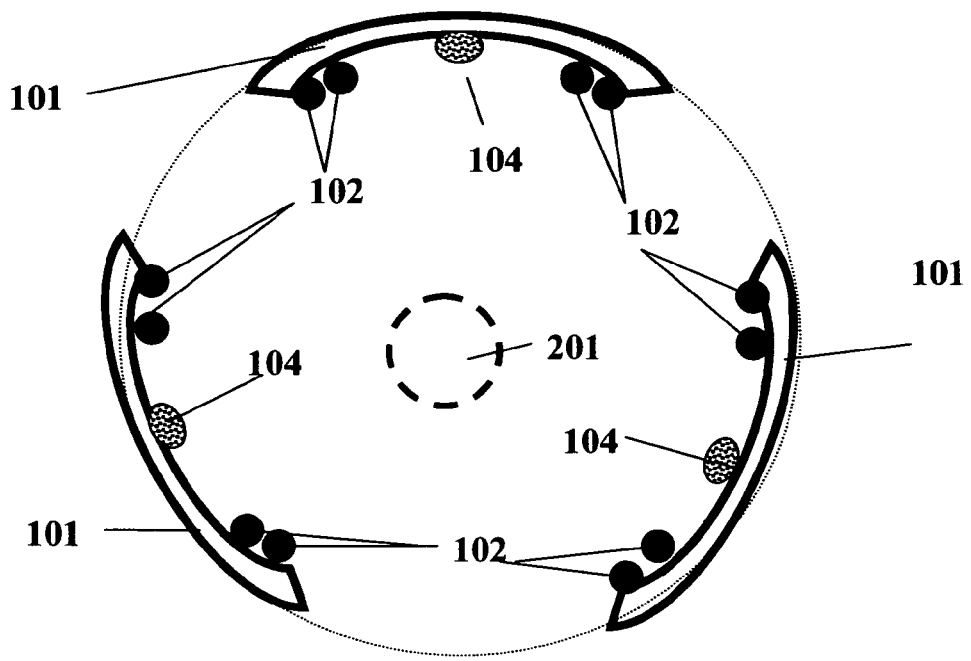
FIG. 5 is a top view of the image-capturing portion of a second embodiment of a portion of an image in accordance with the invention.
Figure 6:
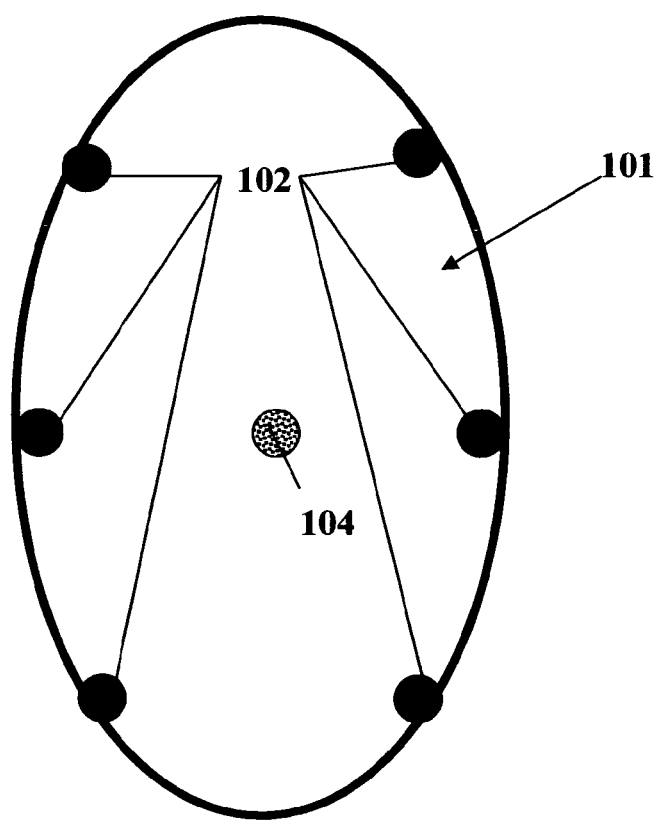
FIG. 6 is a planar view of an image-capturing module utilized in the image-capturing portion shown in FIG. 5.

Turning now to FIG. 5, one embodiment of digitizer 100 that is particularly useful with infant head image capture comprises 18 triangulated digital cameras 102. Cameras 102 are arranged onto three supports or modules 501. Six cameras 102 are located in each module 501. Modules 501 are arranged in an equilateral triangle arrangement with each module 501 located at a vertex. Twelve of the triangulated cameras 102 are used to obtain digital image information regarding the three-dimensional shape of the infant's head 201. The remaining six cameras 102 capture digital photographs (i.e. texture data) of the child. A single projector 104 is located in each of the three modules 501, and projects a random infrared speckle pattern such as shown in FIG. 4 onto the child 201 at the moment the image is taken. This pattern cannot be seen by the operator or the child, but is visible to the 12 cameras 102 that obtain the digital shape information.

Figure 7:
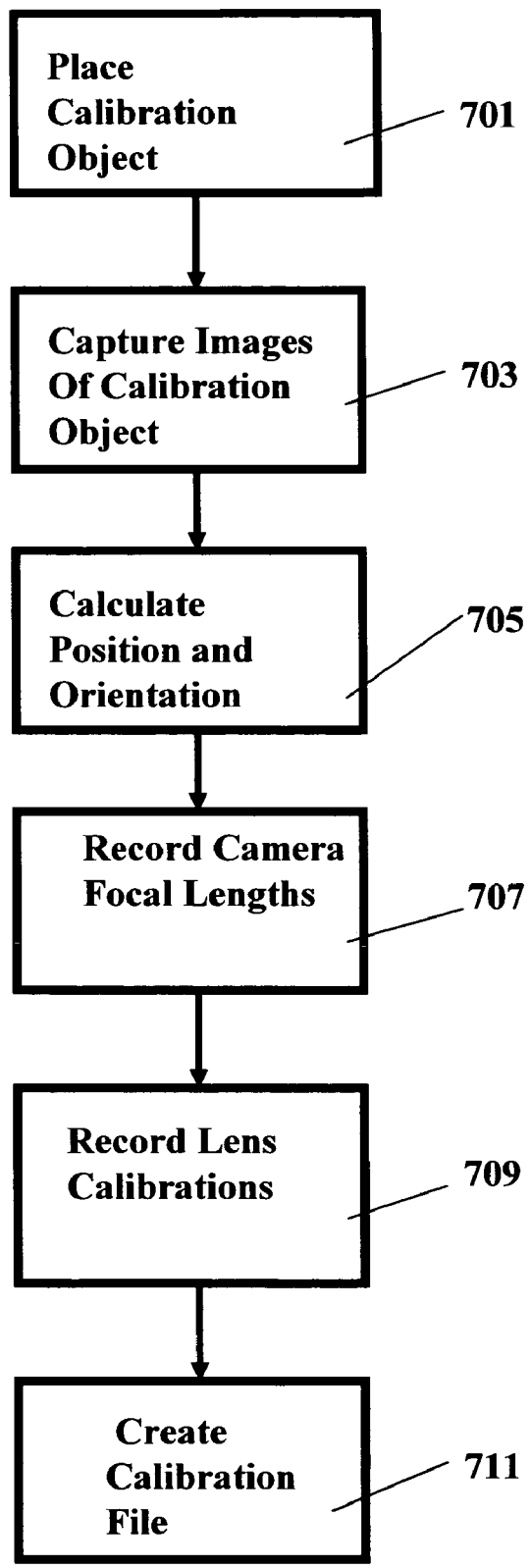
FIG. 7 is a flow diagram of a calibration operation of a system in accordance with the invention.

It is important that the digitizer is calibrated so that the digital data accurately represents the object or infant having its image captured. Turning to FIG. 7, calibration is accomplished by placing a calibration object into the center of the digitizer at step 701 and then operating all of cameras 102 simultaneously with projectors 104 to simultaneously capture 12 images of the object at step 703. At step 705, using the 12 images, along with information about the calibration standard itself, the precise location and orientation of each digital camera 102 with respect to one another is determined. Data regarding each of the camera's focal lengths obtained at step 707, and lens aberration information obtained at step 709 are recorded with the location and orientation data are recorded at step 711 in a calibration file. This calibration file is used later to reconstruct a 3D image of the child from 12 separate digital images.

Figure 8:
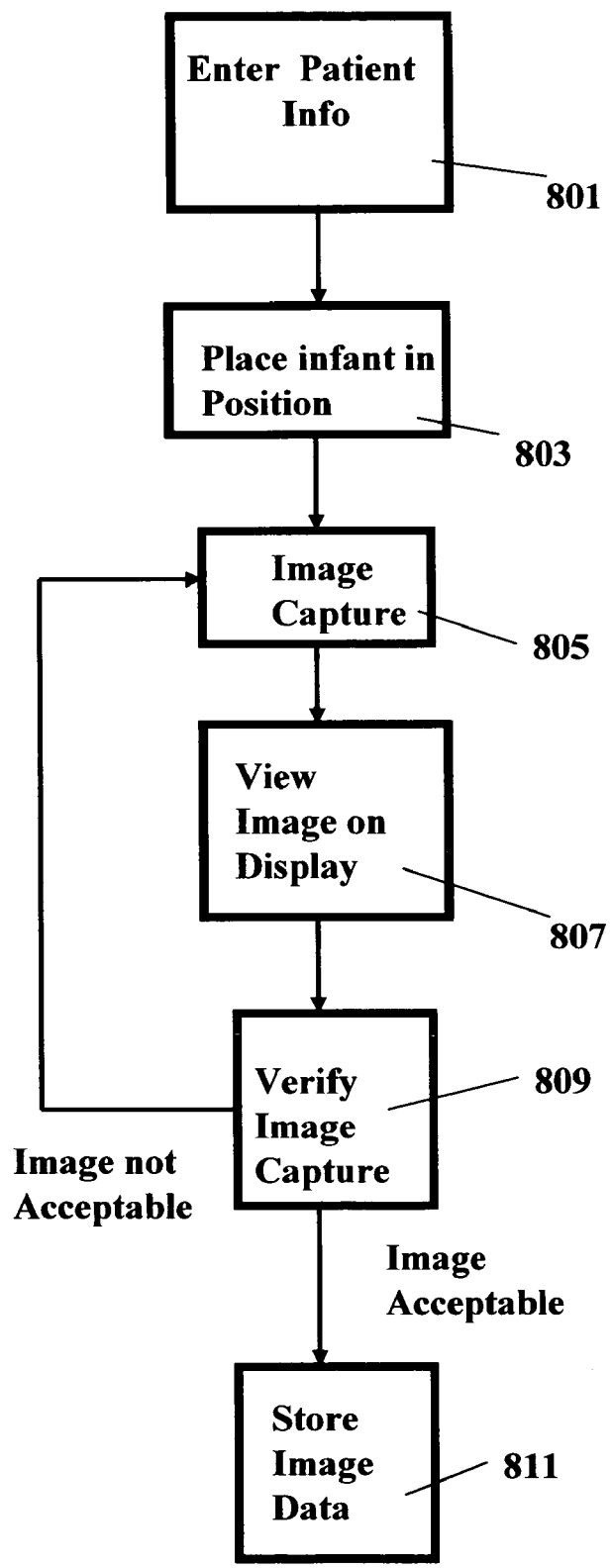
FIG. 8 is a flow diagram of operation of a system in accordance with the invention.

To acquire the infant's image, a system operator first enters the patient information into the digitizer 100 as indicated at step 801 of FIG. 8. The infant is placed into position as indicated at step 803. Both the child 201 and parent are located in the center of the equilateral triangle with the infant sitting on an adjustable, rotating stool. The infant 201 is supported by the parent, who may remain in the system while the child is digitized. The infant's head is not restrained and may move in motion having pivotal, rotational and translation components. When the parent and infant are in position the system operator actuates digitizer 100 to capture and simultaneously record 18 images of the child at step 805. Within two and half minutes, images from the 12 shape cameras are reconstructed into a 360° digital model using the previously recorded calibration data. Texture data (i.e. digital photographs) are automatically overlaid on the model, although the data may be viewed with or without this information. (FIGS. 3–6) Processing the 12 images into a single model can either be done immediately following the acquisition, or several images can be acquired and processed at a later time. Preferably the image is displayed as indicated at step 807 and the image capture is verified at step 809. The image data of the obtained image is stored at step 811. If the image obtained is not acceptable, new images may be captured, displayed and viewed.

Figure 9:
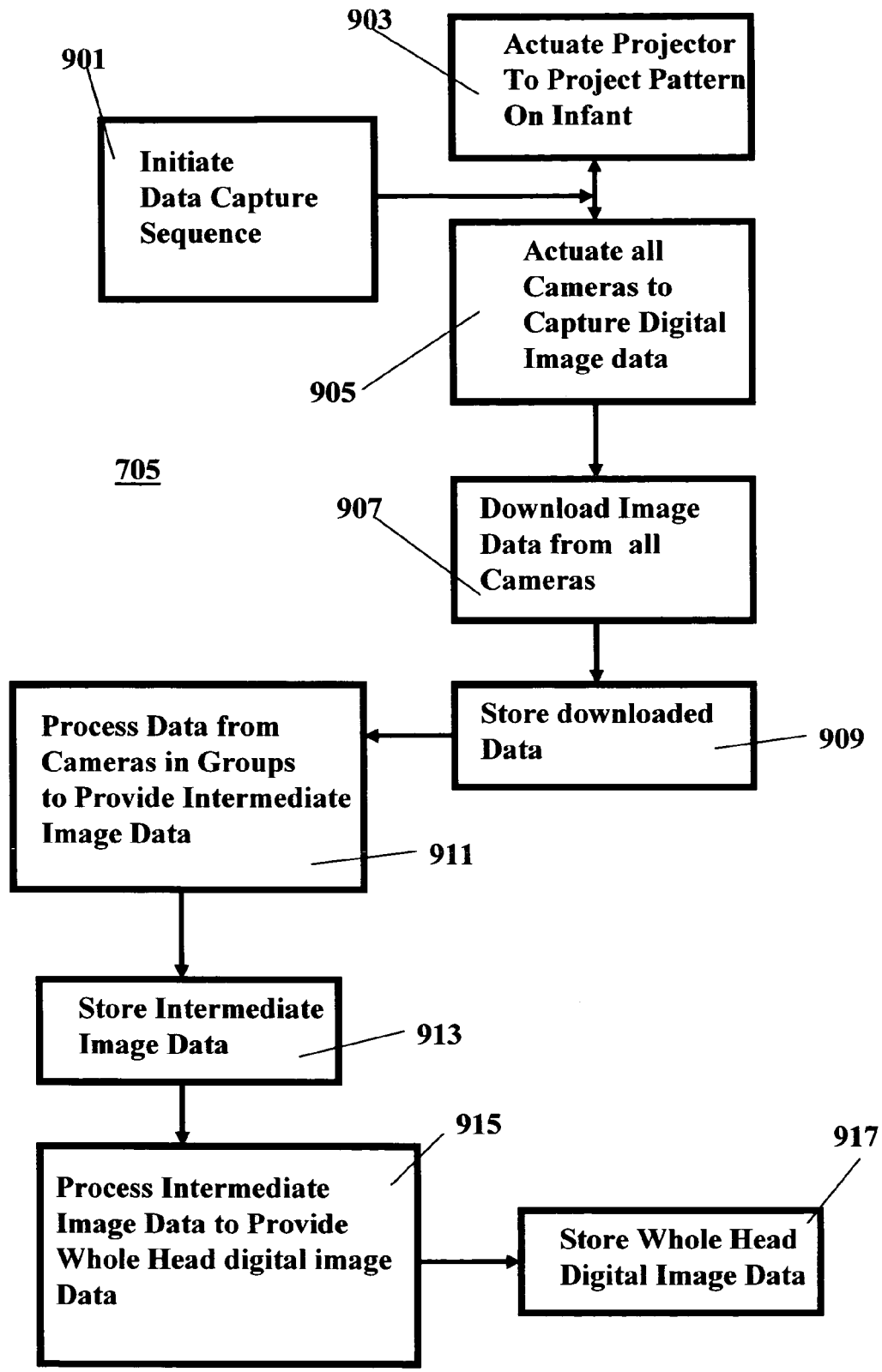
FIG. 9 is a detailed flow diagram of a portion of the flow diagram of FIG. 8.

Turning now to FIG. 9, the operation of digitizer 100 in capturing an image is shown in a more detailed flow diagram. At step 901, image capture is initiated. Simultaneously, all projectors 104 are actuated at step 903 and all cameras 102 are operated at step 904. The resulting digital images are downloaded from all of cameras 102 to processor 105 at step 907 and stored in memory 111 at step 909. The data from cameras 102 in a triangulation pair are processed in accordance with a first algorithm in a program module from memory 109 at step 911 to produce intermediate three-dimensional digital images of corresponding portions of the object or infant's head 201. The intermediate three-dimensional digital images are stored in memory 111 at step 913. Processor 105 then processes the intermediate three-dimensional images at step 915 in accordance with a second algorithm in a program module from memory 109 to produce a complete three-dimensional digital image file for the whole or entire object that is within space 200 or the infant's whole or entire head 201 within space 200. Processor 105 stores the entire three-dimensional image file in memory 111 for later use.

Accuracy is often reported as a 'mean' or 'average' difference between the surfaces, however in this situation reporting an average is inaccurate because the surface created from the new data set may have components that lay both above (+) and below (−) the reference surface. These positive and negative values offset each other resulting in a mean value around zero. In situations where this cancellation can occur, it is necessary to report the mean difference as a Root Mean Square (RMS). The root mean square statistic reports typical magnitudes of deviations without regard for positive or negative values.

By using a best-fit analysis type algorithm to analyze the illustrative digitizer, the RMS mean deviation between the surfaces was calculated to be +/−0.236 mm, with over 95% of the data clearly falling within +/−0.5 mm.

A hazard analysis performed on the system of the invention demonstrates that, system 100 is safe. Digitizer 100 will not cause retinal blue-light or infrared eye injuries.

One advantage of digitizer 100 is that the image acquisition is fast enough so that motion of the infant does not present a problem for image capture, or affect the accuracy of the data acquired. If the image could not be captured 'instantaneously' it would be necessary to fixture or restrain the child in one position in order to ensure there would be no motion artifacts in the data.

Capture of all 18 images (12 shape, 6 texture) is accomplished through utilization of an interface 103 in FIG. 1 that functions single frame grabber circuit board. At image capture time processor 105 generates a signal via interface 103 that is sent out to all cameras 102 to simultaneously record the digital images for processing. Each camera 102 records a digital image at a speed of $1/125^{th}$ of a second (0.008 seconds). This nearly instantaneous capture has allowed us to capture digitized images of infants in motion. The symmetrical placement of the cameras around the periphery also ensures that the child's specific orientation and position within the space 200 is not a factor.

Post-processing of intermediate images into a single digital model is done quickly so that the complete image can be reviewed before allowing the patient to leave the office. In an illustrative embodiment of the system the complete image may be produced in less than three minutes Once processed, the data may be viewed in a variety of formats that include point cloud, wire frame, surface, and texture. As the name implies, the image presented as a point cloud consists of hundreds of thousands of independent single points of data. A wire frame, sometimes referred to as a polygon or triangulated mesh, connects three individual data points into a single polygon with each data point being referred to as a vertex. A wire frame is the first step in viewing the individual data points as one continuous connected 'surface'. Once connected as a series of polygons, mathematical algorithms are applied to convert the faceted, polygonized surface into a smooth continuous surface upon which more complex measurements and mathematical analyses can be performed. While point cloud, wire frame and surface rendering are the most common methods for viewing digital data, it is also possible to obtain texture information which is seamlessly overlaid on the model. Texture data is overlaid onto the digital image to ensure proper patient identification.

The projection of a random infrared pattern by projectors 104, rather than a grid or line pattern, overcomes problems with interference and enables digital capture of the entire infant head or object 201 in a single shot. This includes a 360° image including the face, top of the head, and neck/occipital region all acquired within 0.008 seconds. Digitizer 100 is safe, impervious to motion, does not require the infant to be sedated or restrained, and images can be viewed within 2–3 minutes of acquisition. The digital data can be exported to create physical models using stereo lithography or carved on a 5-axis milling machine. Quantitative data (linear and surface measurements, curvature, and volumes) can also be obtained directly from the digital data.

The three-dimensional images are stored in memory 111 of digitizer 100 as shown in FIG. 1. A sequence of three-dimensional images may be captured and stored in memory 11 for later playback. The three-dimensional images may be sequentially displayed to produce a three-dimensional movie of the infant or object in motion. A particular feature is that since each three-dimensional image is taken of the entirety of the infant's head or object, the view of the image on playback may be changed to observe different portions of the infant's head or object as it moves. The view may be taken from any point on the exterior of the image capture space defined by the digital cameras.

Turning now to FIG. 10, steps 1001 and 1003 are steps that were utilized in the past to produce a custom cranial remodeling device or band for an infant with a deformed head. A positive life size cast is made of an infant's head or a first shape as indicated at 1001. A corresponding modified cast or second shape is then made from which a cranial remodeling band is produced at step 1003. In the past, a cranial remodeling band for the infant is produced by forming the band on the second cast which represents a modified head shape. A library of hundreds of infant head casts and corresponding modified casts has been maintained at the assignee of the present invention and this library of actual head casts and the corresponding modified casts is believed to be a unique resource. It is this unique resource that is utilized to provide databases for developing the method and apparatus of the present invention.

An additional unique resource is that databases of additional information corresponding to each infant have been developed by the assignee of the present invention. That database includes information that identifies the type of cranial remodeling device for each infant head shape as well as the style of the cranial remodeling device and features selected for incorporation into the cranial remodeling device to provide for appropriate suspension and correction of the deformity. Still further, each cranial remodeling device has trim lines that are uniquely cut so as to provide for appropriate suspension and functionality as well as appearance. A further database developed by the assignee of the present invention has trim line data for each cranial remodeling device that has been previously fabricated corresponding to the casts for unmodified heads.

In a first embodiment of the invention, shown as system 1200 in FIG. 11, the databases 1203, 1205 of unmodified shapes and corresponding modified shapes are used by a computer 1201 to train a neural network 1300.

In accordance with one aspect of the invention, each unmodified or first head shape is digitally captured at step 1005 as shown in FIG. 10 by a digitizer 100 shown in FIG. 11, to produce first digital data at step 1007 to provide a complete three dimensional representation of the entirety of a head including the top portion. The first digital data is stored in database 1203 at step 1009. Each corresponding modified or second head shape is digitally captured by digitizer 100 at step 1011 to produce second digital data at step 1013. The second digital data is stored in database 1205 at step 1015. One to one correspondence is provided between each first digital data and the corresponding second digital data as indicated at step 1017. The correspondence between digital data for first and corresponding second head shapes is maintained by utilizing any one of several known arrangements for maintaining correspondence.

In accordance with one aspect of the illustrative embodiment the first and second data stored comprises Cartesian coordinates for a plurality of points on the surface of the corresponding shape.

In the illustrative embodiment shown in FIG. 10, digitizer 100 utilizes a plurality of digital cameras that are positioned to substantially surround the entirety of a cast or a patient's head such that a substantially instantaneous capture of the cast or of the infant's head is obtained. As used herein, the term "digitizer" is utilized to identify a data capture system that produces digital data that represents the entirety of a cast or a head and which is obtained from a substantially instantaneous capture.

Figure 12:
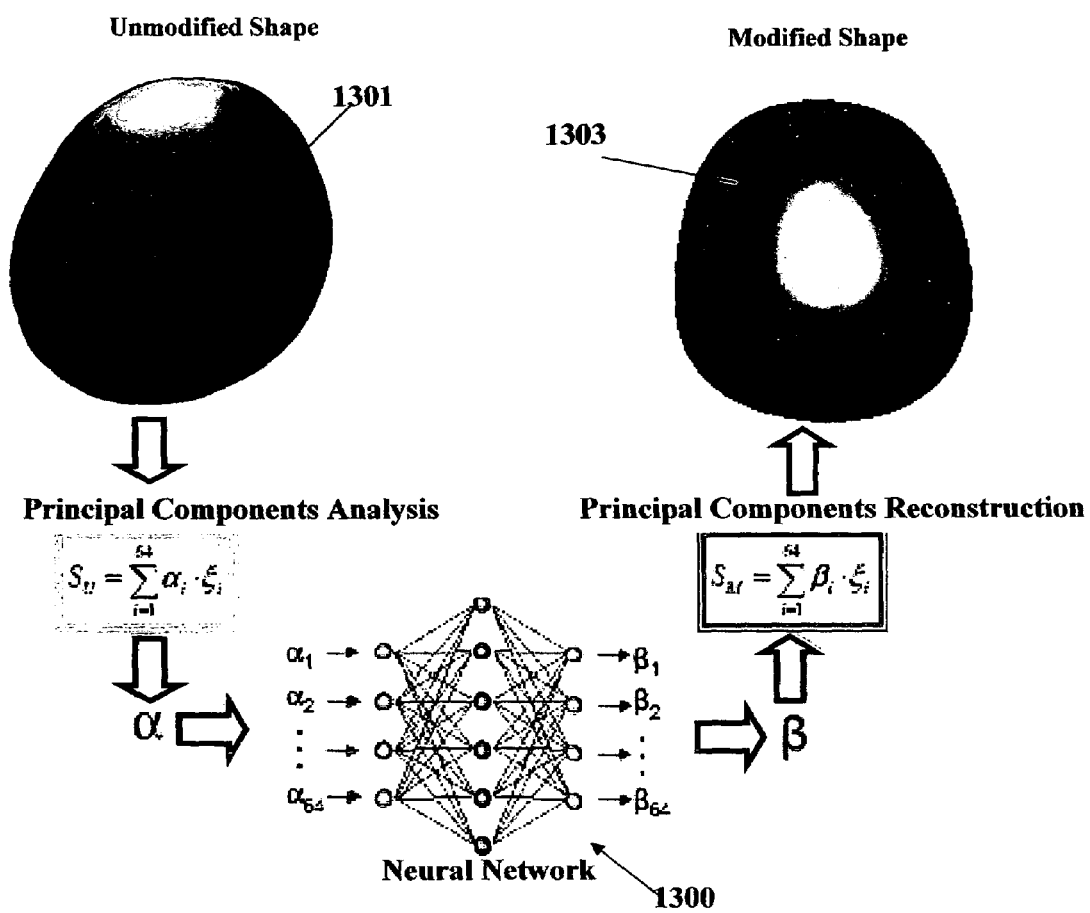
FIG. 12 illustrates use of Principal Components Analysis and neural networks in the illustrative embodiment of the invention.

In accordance with an aspect of the illustrative embodiment of the invention, neural network 1300 is "trained", as explained below, so that captured data of a first or unmodified shape 1301 shown in FIG. 12 which has no corresponding second or modified shape is processed by neural network 1300 to produce a second or modified shape 1303. More specifically, principal components analysis (PCA) is utilized in conjunction with neural network 1300. Neural network 1300 is trained by utilizing captured data for first shapes from database 1203 with corresponding captured data for second shapes from database 1205.

Turning to FIG. 13, operation of system 1200 is shown. At steps 1401 and 1403, one or more databases are provided to store data for a plurality of first or unmodified captured shapes and to store data for a plurality of corresponding second or modified captured shapes.

The data from each captured first and second image is represented using the same number of data points. In addition, all captured images are consistently aligned with each other.

The captured data for all head shapes represented in the databases 1203, 1205 of are aligned in a consistent way. The consistent alignment or image orientation has two separate aspects: alignment of all captured modified images with each other as shown at step 1405; and alignment of each unmodified captured image with the corresponding modified captured image as shown at step 1407. Alignment of unmodified and modified captured images ensures that the neural network will consistently apply modifications. Alignment of the modified captured images with one another allows PCA to take advantage of the similarities between different cast shapes.

The casts from which the captured images are obtained do not include facial details. Typically the face portion is merely a plane. The position of the face plane is really a result of deformity. To align the shapes a manually iterative visualization process is utilized. This approach "solved" half of the alignment issue—aligning all of the modified images with each other so that the principal components analysis could take advantage of the similarities between these shapes.

To align each unmodified captured image with its corresponding captured modified image, alignment of the face planes is was utilized. For the most part, the face planes represent a portion of the shapes that are not modified from the unmodified to the modified head shape and provide consistency. An additional attraction to this approach is that there on the head actual casts, there is writing on the face planes and this writing is visible in the texture photographs that can be overlaid onto the captured images. Alignment of face planes and writing provides a precise registration of the unmodified and modified captured images.

An automated approach to this alignment was developed using several of the first captured images. The automated alignment works where texture photographs are well focused and clear. In other cases automated alignment is supplemented with alignment by selecting "freehand" points on both the modified and unmodified images using commercially available software and then using the registration tool of that software. This approach aligned all unmodified captures with modified captures so that corrections would be consistently applied.

The capture data for both the unmodified and modified head shapes are normalized at step 1409 for training the neural network. As part of the normalization, a scale factor is stored for each for each normalized head or shape set.

As indicated at step 1411, PCA is utilized with the aligned shapes to determine PCA coefficients. Because PCA uses the same set of basis vectors (shapes) to represent each head (only the coefficients in the summation are changed), each captured image is represented using the same number of data points. For computational efficiency, the number of points should be as small as possible.

The original digitized data for first and second shapes stored in databases 1203, 1205 represent each point on a surface using a three-dimensional Cartesian coordinate system. This approach requires three numbers per point; the x, y, and z distances relative to an origin. In representing the head captures, we developed a scheme that allows us to represent the same information using only one number per data point. Mathematically the approach combines cylindrical and spherical coordinate systems. It should be noted that to obtain three dimensional representations of an object, a spherical coordinate system may be utilized. However, in the embodiment of the invention, the bottom of the shape is actually the neck of the infant, and is not of interest.

Conceptually this approach is similar to a novelty toy known as "a bed of nails." Pressing a hand or face against a grid of moveable pins pushes the pins out to form a 3D copy on the other side of the toy. This approach can be thought of as a set of moveable pins protruding from a central body that is shaped like a silo—a cylinder with a hemisphere capped to the top. The pins are fixed in their location, except that they can be drawn into or out of the central body. Using this approach, all that is needed to describe a shape is to give the amount that each pin is extended.

To adequately represent each head shape, a fixed number of approximately 5400 data points are utilized. To represent each of the captures using a fixed number of data points, the distance that each "pin" protrudes is computed. This is easily achieved mathematically by determining the point of intersection between a ray pointing along the pin direction and the polygons provided by data from the infrared imager. A set of such "pins" were selected as a reasonable compromise between accuracy of the representation and keeping the number of points to a minimum for efficiency in PCA. The specific set of points was copied from one of the larger cast captures. This number was adequate for a large head shape, so it would also suffice for smaller ones. A commercially available program used to execute this "interpolation" algorithm requires as input the original but aligned capture data and provides as output the set of approximately 5400 "pin lengths" that represent the shape.

Using the consistent alignment and the consistent array of data points described above, the normalized data for each captured cast was interpolated onto this "standard grid." Computing the covariance matrix produced an n×n matrix, where "n" is the number of data points. As the name implies, this covariance matrix analyzes the statistical correlations between all of the "pin lengths." Computing the eigenvalues and eigenvectors of this large covariance matrix provides PCA basis shapes. The PCA shapes are the eigenvectors associated with the largest 64 eigenvalues of the covariance matrix. This approach of computing basis shapes using the covariance matrix makes optimal use of the correlations between all the data points used on a standard grid.

PCA analysis allows cast shapes to be represented using only 64 PCA coefficients. FIG. 14 sets out the hyper parameters for the 64 PCA coefficients. To transform the unmodified cast shapes into correct modified shapes, it is only necessary to modify the 64 PCA coefficients. For this processing task we selected and provide neural network 300 as indicated at step 413 of FIG. 4.

Neural networks are an example of computational tools known as "Learning Machines" and are able to learn any continuous mathematical mapping.

As those skilled in the art will understand, learning machines such as neural networks are distinguished from expert systems, in which programmers are utilized to program a system to perform the same branching sequences of steps that a human expert would perform. In effect, an expert system is an attempt to clone the knowledge base of an expert, whereas, a neural network is taught to "think" or operate based upon results that an expert might produce from certain inputs.

Figure 15:
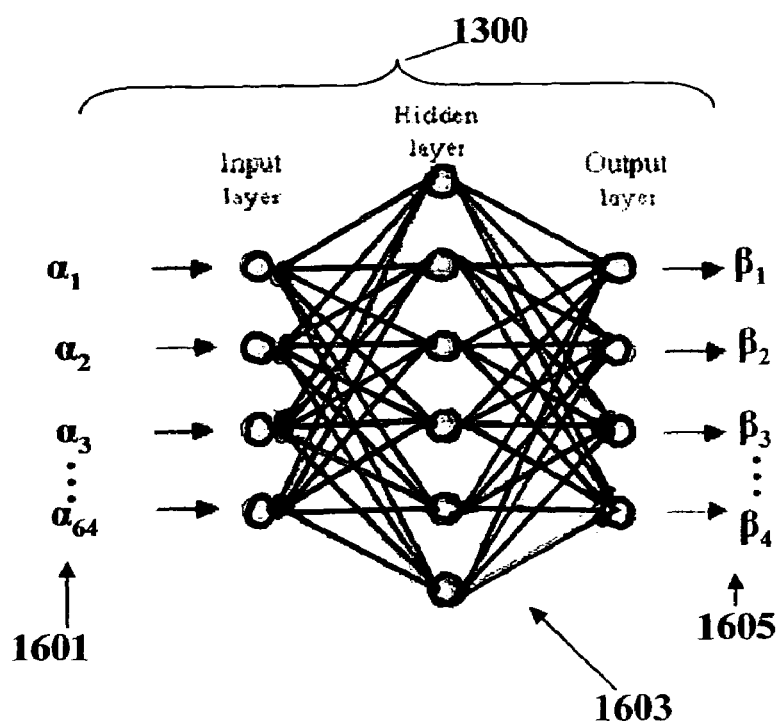
FIG. 15 represents a neural network.

FIG. 15 shows a conceptual diagram of a generic neural network 1300. At a high level, there are three elements of a neural network: the inputs, $\alpha_1$–$\alpha_n$, the hidden layer(s) 1603, and the outputs $\beta_1$–$\beta_n$. A neural network 1300 operates on inputs 1601 using the hidden layer to produce desired outputs 1605. This is achieved through a process called "training."

Neural network 1300 is constructed of computational neurons each connected to others by numbers that simulate strengths of synaptic connections. These numbers are referred to as "weights."

Training refers to modification of weights used in the neural network so that the desired processing task is "learned". Training is achieved by using PCA coefficients for captured data representative of unmodified casts of infant heads as inputs to the network 1300 and modifying weights of hidden layers until the output of the neural network matches PCA coefficients for the captured data representative of corresponding modified casts. Repeating this training thousands of times over the entire set of data representing the unmodified and corresponding captured shapes produces a neural network that achieves the desired transformation as well as is statistically possible. In the illustrative embodiment, several hundred pairs of head casts were utilized to train neural network 1300 at step 1415.

Testing on additional data from pairs of casts that the neural network was not trained with, or "verification testing", was utilized in the illustrative embodiment to ensure that the neural network 1300 has learned to produce the appropriate second shape from first shape captured data and has not simply "memorized" the training set. Once this training of neural network 1300 is complete, as measured by the average least squares difference between the PCA coefficients produced by the network and those from the modified cast shapes, the PCA coefficient weights are "frozen" and the network is simply a computer program like any other computer program and may be loaded onto any appropriate computer.

A commercially available software toolbox was used to develop the learning machine. The particular type of learning machine produced is called a Support Vector Machine (SVM), specifically a Least Squares Support Vector Machine (LS-SVM). Just like the neural networks described above, the SVM "learns" its processing task by modifying "weights" through a "training" process. But in addition to weights, the LS-SVM requires a user to specify "hyper parameters." For the radial basis function (RBF) type of LS-SVM used in this work, there are two hyper parameters: ã (gamma) and ó (sigma). The relative values of these parameters control the smoothness and the accuracy of the processing task. This concept is very similar to using different degree polynomials in conventional curve fitting.

Figure 16:
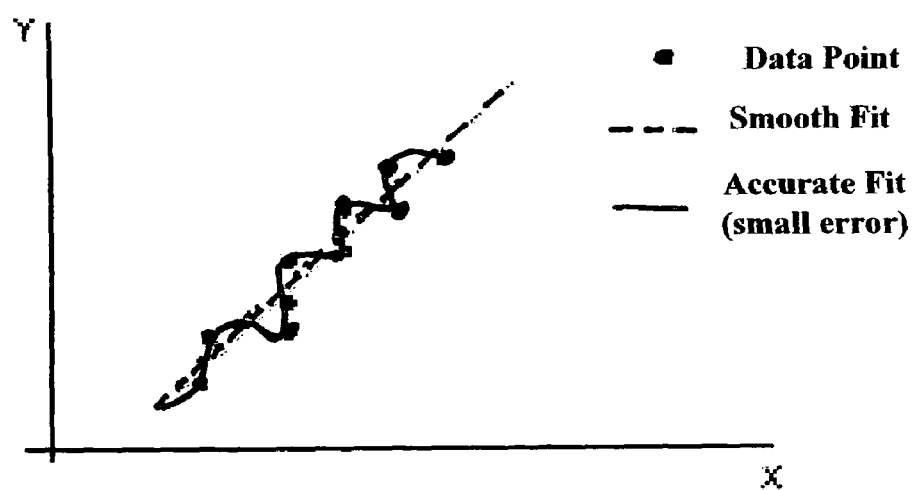
FIG. 16 is a graph.

FIG. 16 shows a curve-fitting task in two dimensions for easy visualization. Because there are a finite number of data points, (x, y)-pairs, it is always possible to achieve perfect accuracy by selecting a polynomial with a high enough degree. The polynomial will simply pass through each of the data points and bend as it needs to in between the data where its performance is not being measured. This approach provides ridiculous results in between the data points and is not a desired result. One solution to this problem is to require that the curve defined by the polynomial be smooth i.e., to not have sharp bends. This solution is fulfilled in the LS-SVM using ã and ó. Higher values of ó correspond to smoother curves and higher values of a produce greater accuracy on the data set.

An unmodified or first shape represented by captured data is processed utilizing a principal components analysis algorithm. The resulting PCA representation is processed by a neural network 1300 to produce a second or modified PCA representation of a modified shape.

In the system of the illustrative embodiment of the invention cross-validation was used to choose the hyper-parameters. Data is randomly assigned to four groups. Three of the four groups were used to train the LS-SVM, and the remaining set was used to measure the performance in predicting the PCA coefficients for the modified head shapes. In turn, each of the four groups serves as the test set while the other three are used for training. The group assignment/division was repeated two times, so a total of eight training and test sets were analyzed (four groups with two repetitions). This process was repeated for a grid of (ã, ó)-pairs ranging from 0–200 on both variables. The range was investigated using a 70×70 grid of (ã, ó)-pairs, so a total of 4900 neural nets were tested for each of the first 38 PCA coefficients. From this computationally intensive assessment, hyper-parameters were determined and validated for the first 38 PCA coefficients and extrapolated those results to select hyper-parameters for the remaining 26. Further "tuning" of the remaining 26 PCA hyper-parameters is unlikely to produce significant improvement in the final results because the first PCA coefficients are the most influential on the solution. The table shown in FIG. 14 presents the results for the hyper-parameter tuning.

Once hyper parameters were tuned, the LS-SVM models generally produced errors of less than two percent for the PCA coefficients of the modified casts in test sets (during cross-validation). Applying these tuned models to head casts that were not part of the cross-validation or training sets also generated excellent results.

There is a surprising variability of the head shapes as represented by cast shapes. Modified casts are not simply small changes to a consistent "helmet shape." Each is uniquely adapted to the unmodified shape that it is intended to correct. Being so strongly coupled to the unmodified shapes makes these modified casts surprisingly different from one another. Of the several hundred casts that we analyzed, each is unique.

Interpolating the aligned shapes also provided surprises and challenges. The "bed of nails" concept is very effective in reducing the size of the data sets and providing a consistent representation for PCA. It helps reduce the number of data sets that would have otherwise been required to train a larger neural network. Instead of representing each data point by three components, each data point is represented by one component thereby reducing the number of data sets significantly. By utilizing this approach, the process is speeded up significantly.

Returning to FIG. 13, at step 1415, neural network 1300 is trained as described above. Once neural network 1300 is trained, it is then utilized to operate on new unmodified heads or shapes to produce a modified or second shape as indicated at step 1417.

Figure 17:
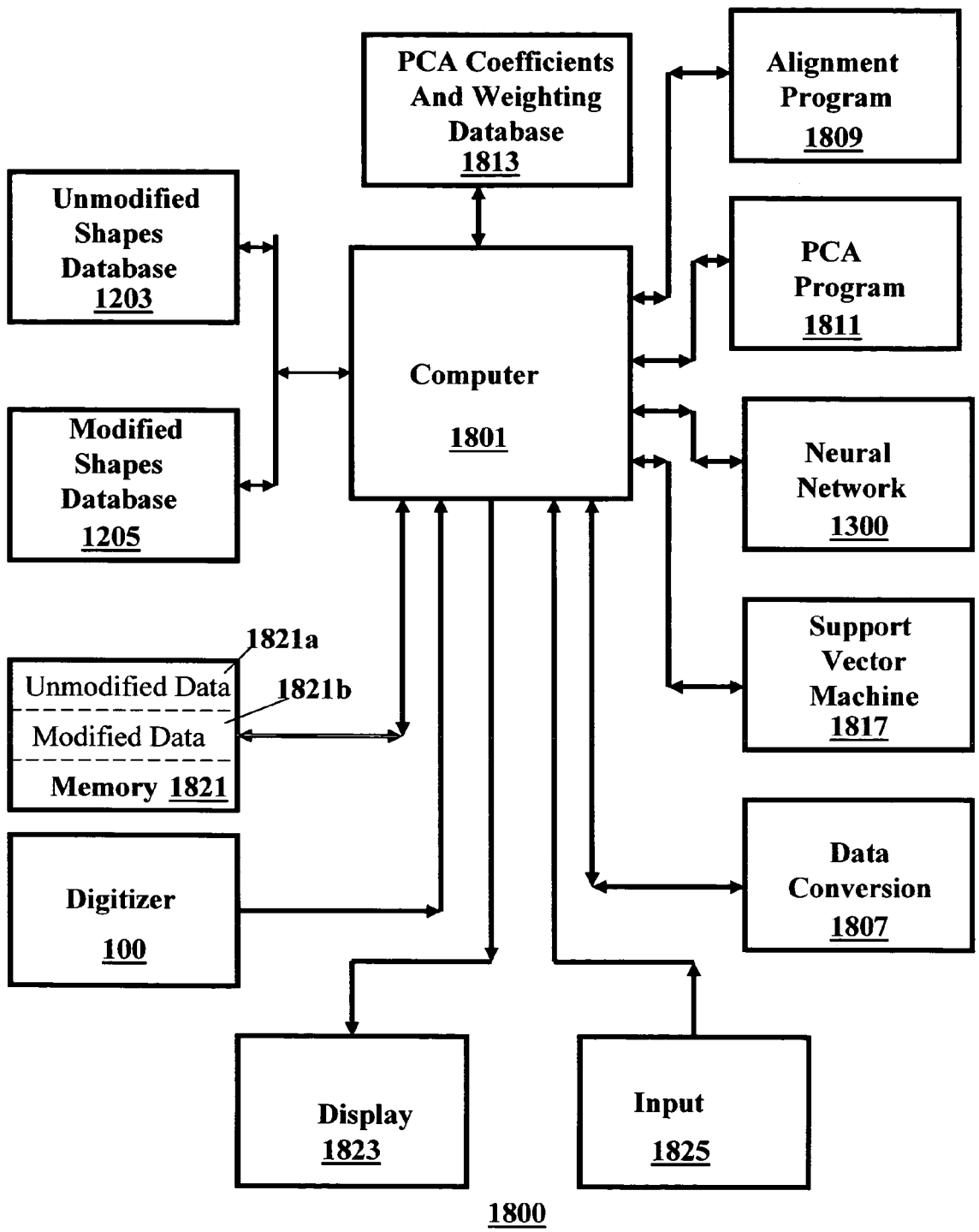
FIG. 17 is a block diagram of a system in accordance with the principles of the invention.

Turning now to FIG. 17, a block diagram of a system 1800 in accordance with the principles of the invention is shown. System 1800 is utilized to both train a neural network 1300 described above and then to utilize the trained neural network 1300 to provide usable modified head shapes from either casts of deformed head shapes or directly from such an infant's head.

System 1800 includes a computer 1801 which may any one of a number of commercially available computers. Computer 1801 has a display 1823 and an input device 1825 to permit visualization of data and control of operation of system 1800.

Direct head image capture is a desirable feature that is provided to eliminate the need to cast the children's head. An image capturing digitizer 100 is provided that provides substantially instantaneous image captures of head shapes. The digitized image 1821a is stored in a memory 1821 by computer 1801. Computer 1801 utilizes a data conversion program 1807 to normalize data, store the normalized data in memory 1821 and its scaling factor, and to convert the normalized, captured data to "bed of nails" data as described above. Computer 1801 stores the modified, normalized data 1821b in memory 1821. Computer 1801 utilizing an alignment program 1809 to align modified data 1821b to an alignment consistent with the alignments described above and to store the aligned data in an unmodified shapes database 1803. Computer 1801 obtains PCA coefficients and weightings from a database 1813 and utilizes neural network 1300 and a support vector machine 1817 to operate on the data for a first shape stored in memory 1821a to produce data for a modified or second shape that is then stored in memory 1821b. The data for the modified shape stored in memory 1821b may then be utilized to fabricate a cranial remodeling device or band for the corresponding head.

Figure 18:
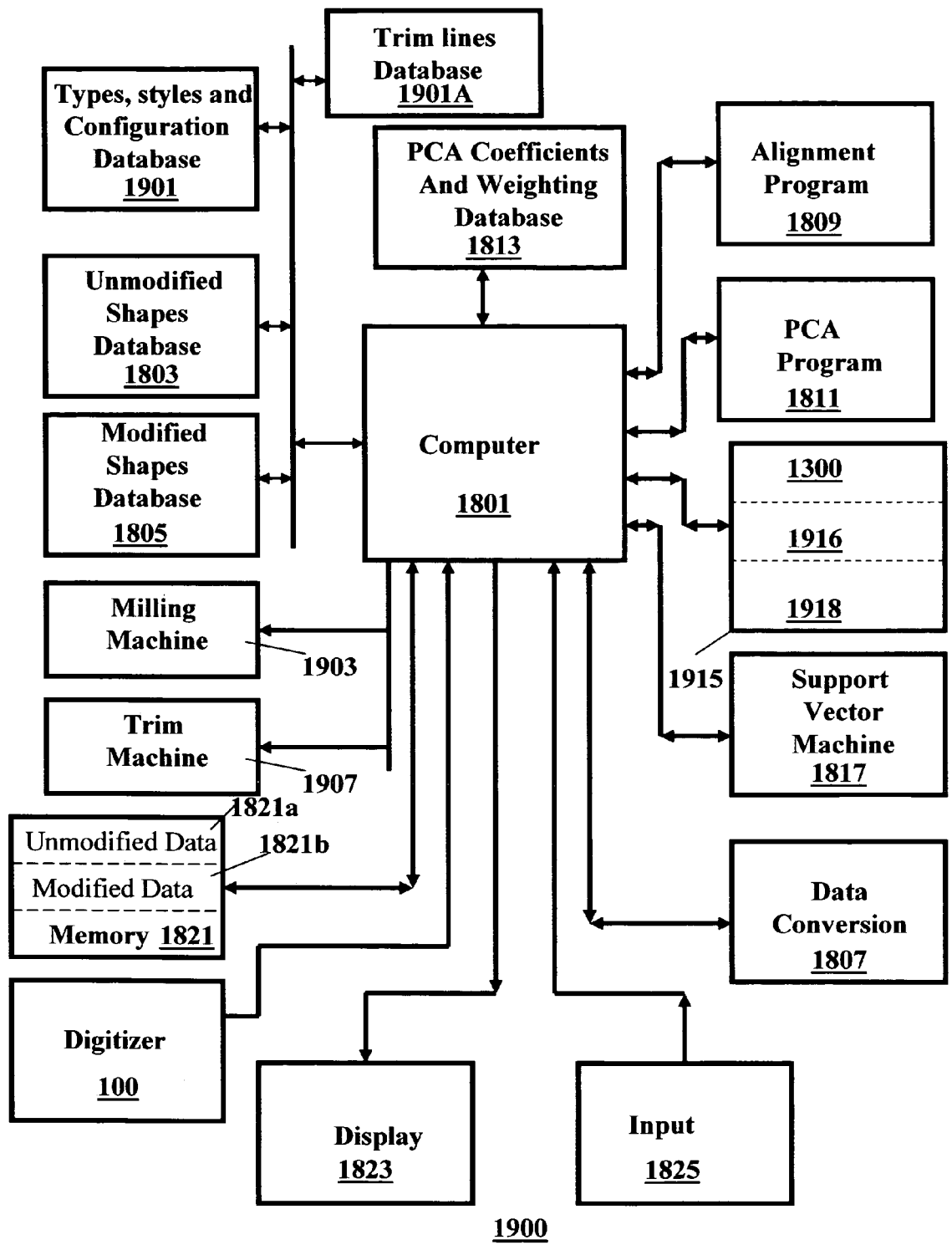
FIG. 18 is a block diagram of another system in accordance with the principles of the invention.

In another embodiment of the invention, shown in FIG. 18, a system 1900 is also "trained" such that in addition to producing a modified head shape that is utilized for fabrication of a cranial remodeling band, system 1900 additionally determines a type and style of the cranial remodeling device or band which is particularly appropriate for the deformity as well as a configuration for the device or band. The type and style of device is determined, in part, from the nature and extent of the cranial deformity and/or from the fit and function of the cranial remodeling band to correct the cranial deformity.

The type of remodeling device or band is selected based upon the nature of the deformity. In the illustrative embodiment of the invention, the band types may be classified as Side-Opening, Brachy Band®, or Bi-Cal™.

The DOC Band® or side-opening type is used primarily to treat children with plagiocephaly, or asymmetrical head configurations. It applies forces in a typically diagonal fashion. A representative side-opening band is described in U.S. Pat. No. 5,094,229 which is incorporated herein by reference.

The Brachy Band® is used to treat brachycephaly, or deformations where the head is too wide, and too short. It applies forces on the lateral prominences and encourages growth of the head in length. This returns the head to a more normal cephalic index (length to width ratio). An example of a Brachy Band is shown in U.S. Pat. No. Re 36,583 which is incorporated herein by reference.

The Bi-Cal™ type is used to treated scaphocephaly, or deformations where the head is too long, and too narrow. It applies forces on the forehead and back of the head and encourages growth of the head in width. This returns the head to a more normal cephalic index (length to width ratio)

In the illustrative embodiment of the invention, the style of band or device includes: RSO or right side opening cranial remodeling band; WRSO or wide right side opening cranial remodeling band; LSO or left side opening cranial remodeling band; WLSO or wide left side opening cranial remodeling band.

The configuration of the devices is selected to provide specific functional attributes. Examples of such attributes include: suspension; application of corrective forces; and protection. Suspension refers to those design configuration features that help to maintain the band in its proper orientation so that the corrective forces are applied where they need to be. In some cases, the design features themselves are used to apply corrective forces which could not be achieved without their inclusion. In some cases, the features are there to protect a surgical site. An example of this would be a strut that goes over the top of the head in the bi-cal band.

Typical features include: use of anterior corners (unilateral or bilateral), posterior corners (unilateral or bilateral), fractional anterior tops, fractional posterior tops, opposing corners, struts, or various combinations of each. It is not possible to generically categorize each feature, e.g., anterior corner, ¼ posterior top, etc, as only used to provide a single function. In some instances, the features are multi-functional, for example providing both suspension and a corrective force.

In the illustrative embodiment of the invention, the "features" include standardized structural configurations which are referred to as: RAC or right anterior corner; LAC or left anterior corner; RPC or right posterior corner; LPC or left posterior corner; a fractional or no anterior or posterior cap; and a partial or full strut across the top of band.

The features may be combined in any number of combinations, but the most common would be what is referred to as an "opposing corners" combination. An example of this would be a right side opening band that also has both a right anterior corner (RAC) and a left posterior corner (LPC). These features are not for aesthetics, but rather represent function improvements to the band for both suspension and application of corrective forces.

It is difficult, if not impossible, to identify what type of cranial remodeling device or band and its features should be for a patient if only information of the corrected shape is provided.

In the past, the type of cranial remodeling device or band, and the additional features that should be incorporated were determined in the past during the modification process. Thus when a head cast is being modified to produce a modified cast, a determination is made as to both the necessary style of the band to be used and the features that should be incorporated into the band. Both the selection of the type of device or band as well as the features to be incorporated are a function of both the original deformity as well as the corrected head shape. The features selected are not independent.

In system 1900, a database 1901 includes for each unmodified head shape dataset data identifying the type and style of cranial remodeling device as well as configuration features.

In system 1900, neural networks 1915 include neural network 1300 trained to provide modified shape data from unmodified shape data as described with respect to system 1800. In addition neural networks 1915 includes neural network 1916 that is trained to select a type and style of cranial remodeling device and to select a configuration of the cranial remodeling device.

Figure 25:
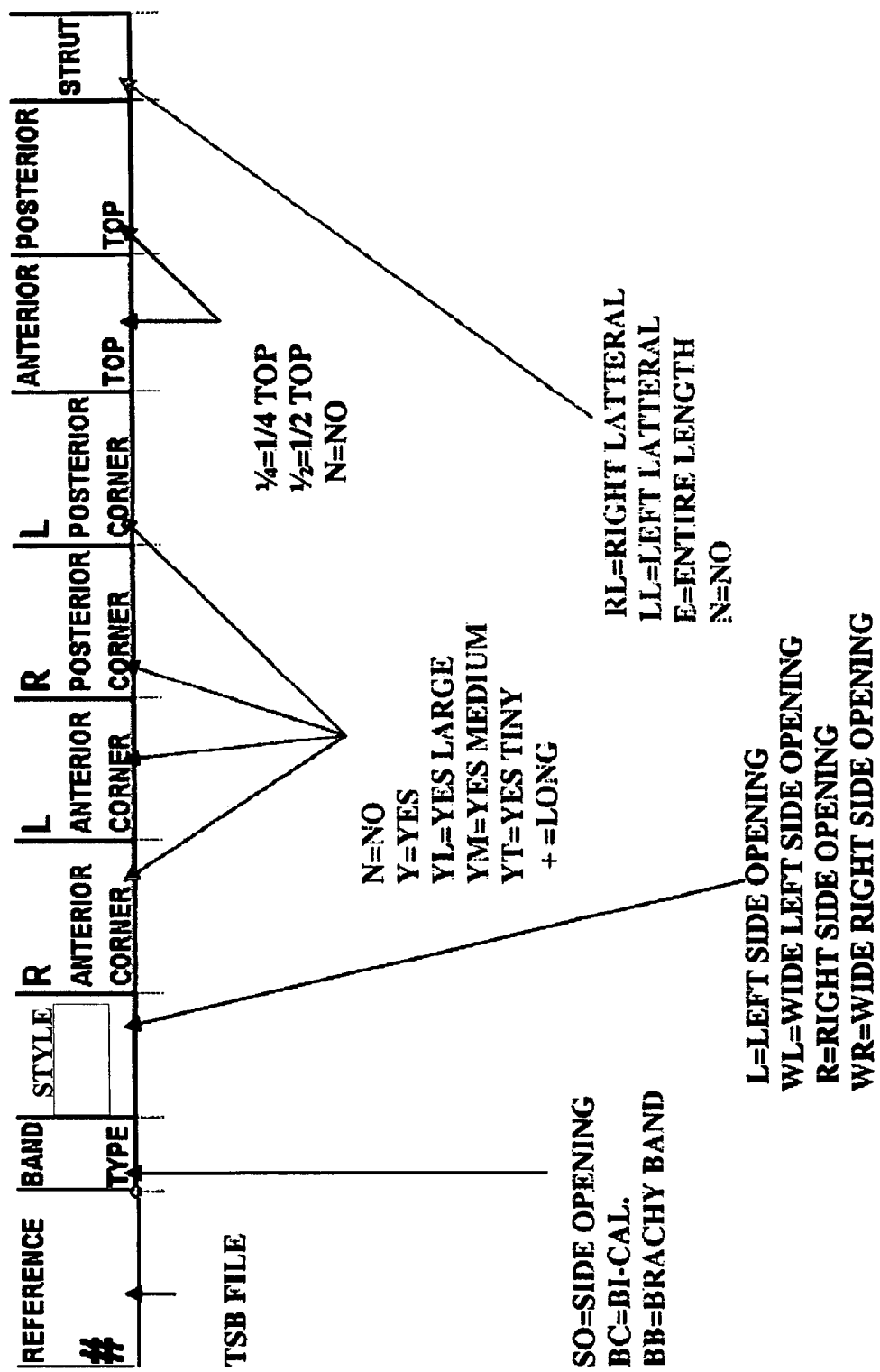
FIG. 25 illustrates a data base format in accordance with the principles of the invention.

Turning now to FIG. 25, the type, style and configuration data entry format stored in database 1901 for each head is shown. Each database entry includes a reference file number to assist in correlating to the corresponding head shape in database 1803. Each database entry also includes an entry field for a band type, an entry field for a band style, four entry fields for each of the right and left anterior corners and right and left posterior corners, a field for identification of a fractional anterior top, a field for identification of a fractional posterior top, and a field for identification of a strut.

Figure 19:
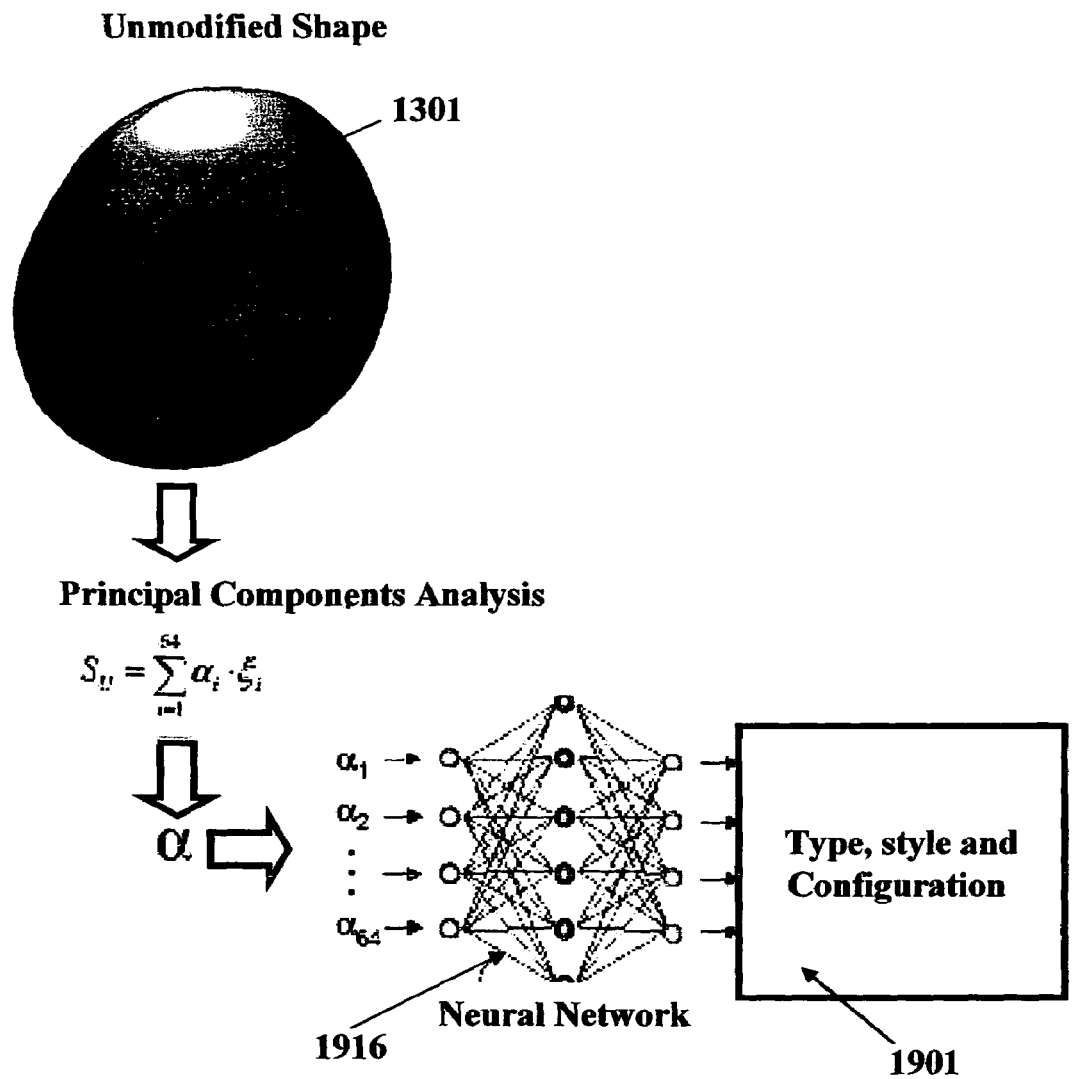
FIG. 19 illustrates training a neural network in accordance with another aspect of the invention.

The methodology for training the neural networks 1916 is similar to that used in the first embodiment. Turning now to FIG. 19, data for unmodified head shapes obtained from database 1203 and corresponding type, style and configuration data for cranial remodeling devices from database 1901 are utilized to train neural network 1916 such that neural network 1916 will automatically select the type, style and configuration data for a cranial remodeling device.

By providing neural networks 1915 trained to generate data representative of a corrected head shape and to select a corresponding cranial remodeling band and features, a highly automated cranial remodeling band fabrication system is provided by system 1900.

System 1900 includes a milling machine 1903 that receives data from computer 1801 and mills a model. Milling machines are commercially available that will receive digital data from a computer or other digital data source and which produce a milled three dimensional object. In system 1900 milling machine 1903 is one such commercially available milling machine. In operation system 1900 instantaneously captures three dimensional image data of an infant's head utilizing digitizer 1819. Computer 1801 stores the captured data 1821a in memory 1821. Computer 1801 then utilizes data conversion module 1807 to convert the data into a "bed of nails" equivalent data and to provide alignment of the captured image and to restore the converted and aligned data in memory 1821. Computer 1801 utilizes neural network 1300 in conjunction with the converted and aligned data of the captured image to produce corresponding three dimensional image data for a modified or second head shape. The three dimensional data 1821b for the modified or second head shape is stored in memory 1821. In addition, neural network 1916 is also utilized to select a corresponding cranial remodeling band type, style and configuration which are likewise stored in memory 1821.

Computer 1801 then utilizes the three dimensional data 1821b for the modified shape to command and direct milling machine 1903 to produce an accurate three dimensional model of the modified shape represented by data 1821b.

Computer 1801 also retrieves corresponding cranial remodeling band type, style and configuration features which are displayed on display monitor 1823 to assist in fabricating a cranial remodeling band for the infant whose head was digitally captured.

In another embodiment of the invention, once the milling machine 1903 has produced a three dimensional representation of a modified head based upon data provided by computer 1801, a copolymer shell is vacuum formed on the representation of the head. The copolymer shell is then shaped to produce the particular device type, style and configuration in a further digital controlled machine 1907.

To summarize, an infant having a deformed head that requires treatment with a cranial remodeling band may have his or her head shape digitally captured by system 1900. System 1900 may be utilized to automatically produce a three dimensional representation of the infant's head shape modified to produce a cranial remodeling band to correct for the head deformities. System 1900 further may be operated to automatically provide an operator with information pertaining to the appropriate configuration and features to be provided in the cranial remodeling band.

Figure 20:
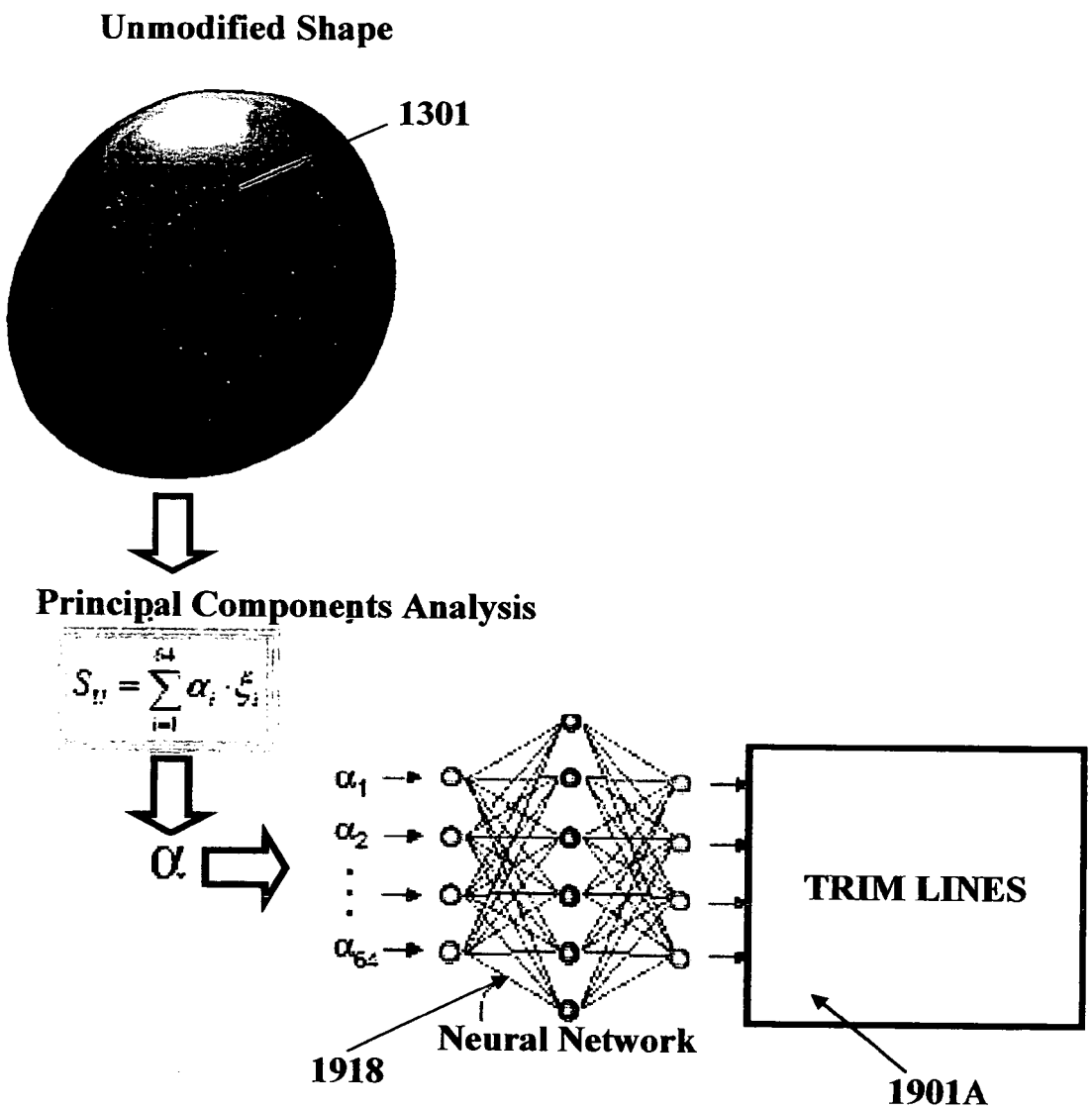
FIG. 20 illustrates training a neural network in accordance with yet another aspect of the invention.

In accordance with yet another aspect of the present invention, in addition to data relating to the band type, style and configuration features, the data may include data for trim lines for cranial remodeling bands. A neural network 1918 included with the neural networks is trained in the same manner that neural network 1916 is trained with trim line data as illustrated in FIG. 20. By including data for trim lines, in database 1901A and utilizing neural network 1916 to also learn the trim lines to be utilized in various cranial remodeling bands, system 1900 produces a cranial remodeling band of an appropriate configuration and having appropriate features, and appropriate trim lines all without any significant human intervention.

Figure 21:
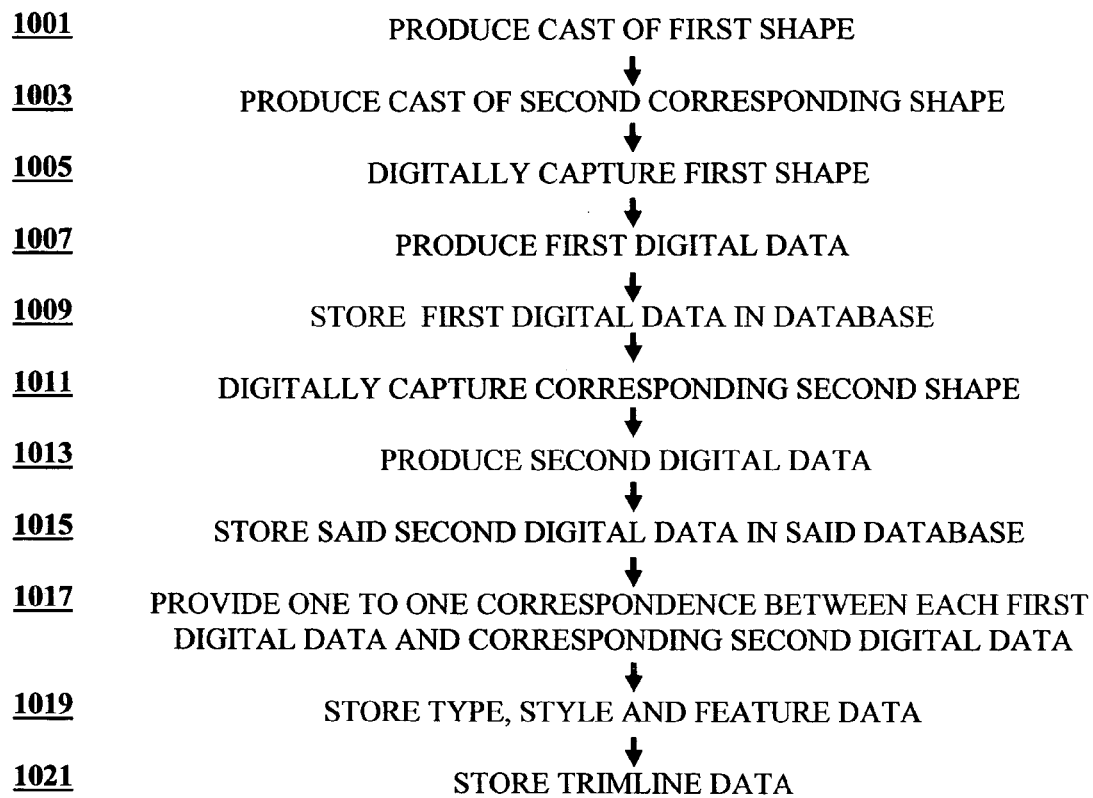
FIG. 21 illustrates a portion of the method utilized in the system of FIG. 18.

FIG. 21 illustrates the method of storing cranial remodeling device type style and feature data and trim line data. FIG. 21 is similar to the flow diagram of FIG. 10 with the additional step of storing in a database cranial remodeling device type, style and configuration feature data corresponding to first digital data at step 1019. FIG. 21 also illustrates the step of storing in a database trim line data for cranial remodeling devices corresponding to first digital data at step 1021.

Neural network 1916 is thus trained to automatically generate trim lines. Once generated, trim line data may be utilized to actually mill trim lines right onto the copolymer cranial band vacuum formed onto that three dimensional representation of a modified head either utilizing milling machine 1903 or machine 1907. Machine 1907 may be a laser trimming machine.

Figure 23:
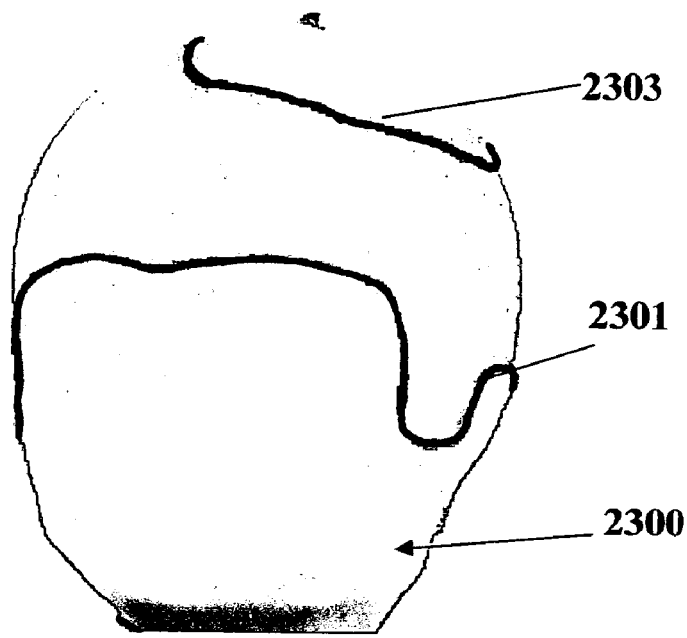
FIG. 23 illustrates a cast of a modified head with trim lines for a cranial remodeling band marked shown thereon.
Figure 24:
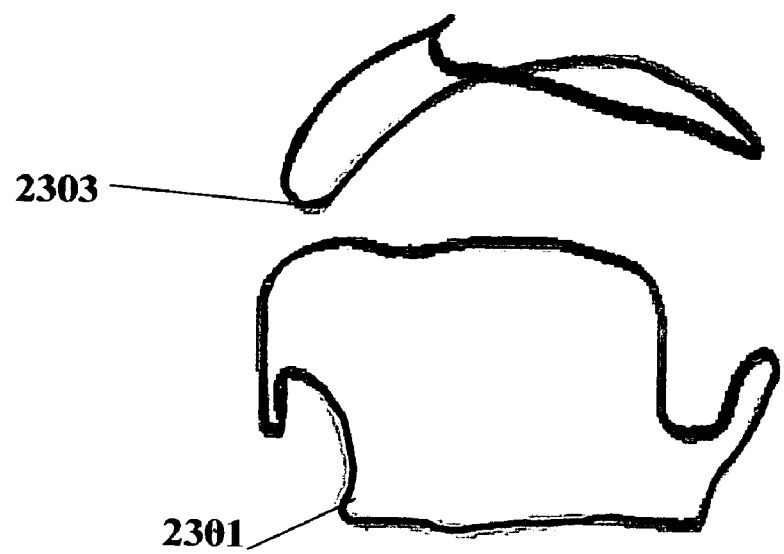
FIG. 24 shows the trim lines of FIG. 22 without the cast.

FIGS. 23 and 24 illustrate exemplary trim lines for a cranial remodeling band. In FIG. 23 trim lines 2301, 2303 are shown on a modified head shape 2300. To better see the trim lines 2301, 2303, FIG. 23 shows the trim lines 2301, 2303 for the cranial remodeling band without head shape 2300. Trim line 2301 illustrates the lower margin of cranial remodeling device or band for head shape 2300 and trim line 2303 illustrates the upper margin of the cranial remodeling band.

Figure 22:
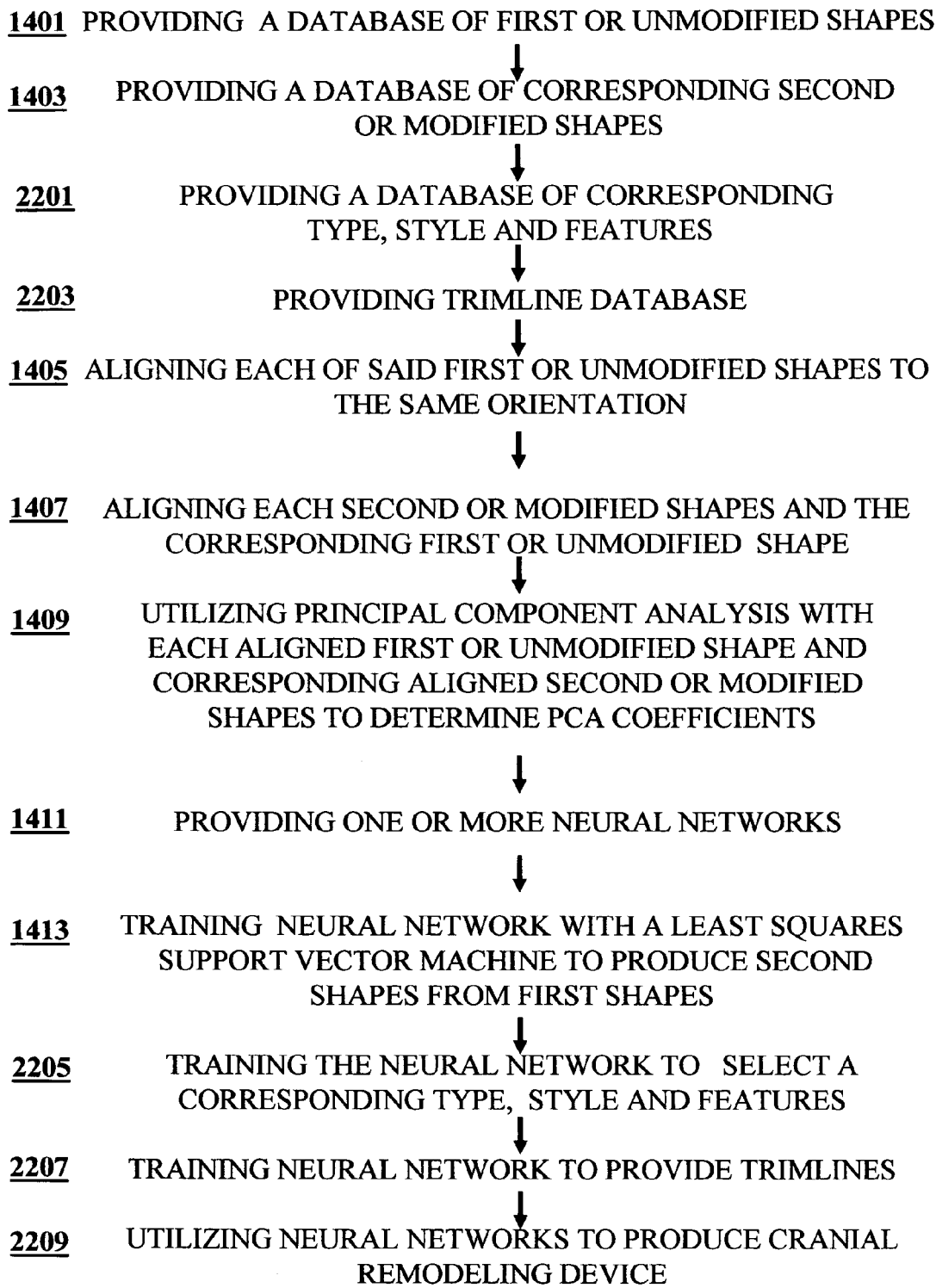
FIG. 22 illustrates other aspects of the method utilized in the system of FIG. 18.

FIG. 22 illustrates the method of training system 1900. The method of FIG. 22 is similar to the method of FIG. 13. At step 2201*a* database of cranial remodeling device type, style and configuration feature data is provided. At step 2203*a* database of trim line data is provided. At step 2205*a* neural network is trained to select cranial remodeling device type, style and configuration features. At step 2207, a neural network is trained to select trim lines for the cranial remodeling device. At step 2209, the trained neural networks are utilized to produce a cranial remodeling device.

It will be appreciated by those skilled in the art that a system 1900 in accordance with the principles of the invention may be configured to automate various aspects of producing cranial remodeling devices automatically and ranging from automatic production of three dimensional representations of head shapes modified to shapes that permit the forming of an appropriate cranial remodeling band to automatic production of cranial remodeling bands to be utilized in the correction of head shape abnormalities.

The invention has been described in terms of illustrative embodiments. It will be apparent to those skilled in the art that various changes and modifications can be made to the illustrative embodiments without departing from the spirit or scope of the invention. It is intended that the invention include all such changes and modifications. It is also intended that the invention not be limited to the illustrative embodiments shown and described. It is intended that the invention be limited only by the claims appended hereto.

What is claimed is:

1. A system comprising:
   a digitizer for substantially instantaneously capturing a three dimensional image of a head and producing first data representative of said image; and
   one or more computers, operable in response to said first data to automatically control manufacture of a wearable device for said head.

2. A system in accordance with claim 1, wherein:
said wearable device is a customized device unique to said head.

3. A system in accordance with claim 2, wherein:
said one or more computers automatically selects a configuration for said wearable device in response to said first data.

4. A system in accordance with claim 2, wherein:
said one or more computers automatically selects trim lines for said wearable device.

5. A system in accordance with claim 1, comprising:
fabrication apparatus responsive to said one or more computers for manufacturing said wearable device.

6. A system in accordance with claim 5, wherein:
said fabrication apparatus comprises milling apparatus to produce a custom form on which said wearable device is formed.

7. A system in accordance with claim 5, wherein:
said fabrication apparatus comprises vacuum apparatus for forming a plastic material.

8. A system in accordance with claim 5 wherein:
said fabrication apparatus comprises trimming apparatus.

9. A system in accordance with claim 1, wherein:
said one or more computers is responsive to said first data to automatically select a device type for said wearable device.

10. A system in accordance with claim 1, wherein:
said one or more computers is responsive to said first data to automatically select a device style for said wearable device.

11. A system in accordance with claim 1, wherein:
said one or more computers is responsive to said first data to automatically select a device type and a device style for said wearable device.

12. A system in accordance with claim 1, wherein:
said head is an infant's head; and
said wearable device comprises a cranial remodeling device.

13. A system in accordance with claim 12, wherein:
said cranial remodeling device is a customized cranial remodeling device unique to said infant's head.

14. A system in accordance with claim 13, wherein:
said one or more computers automatically selects a cranial remodeling device type and style in response to said first data.

15. A system in accordance with claim 14, wherein:
said one or more computers automatically selects features for said cranial remodeling device.

16. A system in accordance with claim 12, wherein:
said one or more computers automatically selects trim lines for said cranial remodeling device.

17. A system in accordance with claim 12, comprising:
fabrication apparatus responsive to said one or more computers for manufacturing said cranial remodeling device.

18. A system in accordance with claim 17, wherein:
said fabrication apparatus comprises milling apparatus to produce a custom form on which said cranial remodeling device is formed.

19. A system in accordance with claim 18, wherein:
said fabrication apparatus comprises vacuum apparatus for forming a plastic material on said custom form.

20. A system in accordance with claim 19, wherein:
said fabrication apparatus comprises trimming apparatus.

21. A system in accordance with claim 17, wherein:
said one or more computers is responsive to said first data to select a cranial remodeling type for said cranial remodeling device.

22. A system in accordance with claim 17, wherein:
said one or more computers is responsive to said first data to select a cranial remodeling style for said cranial remodeling device.

23. A system in accordance with claim 17, wherein:
said one or more computers is responsive to said first data to select a cranial remodeling type and style for said cranial remodeling device.

24. A method comprising:
utilizing a digitizer to substantially instantaneously capturing a three dimensional image of a head and to produce first data representative of said image; and
providing one or more computers operable in response to said first data to automatically control manufacture of a wearable device for said head.

25. A method in accordance with claim 24, wherein:
said wearable device is a customized device unique to said head.

26. A method in accordance with claim 25, comprising:
automatically selecting a configuration for said wearable device in response to said first data.

27. A method in accordance with claim 25, comprising:
automatically selecting trim lines for said wearable device.

28. A method accordance with claim 24, comprising:
providing fabrication apparatus responsive to said one or more computers for manufacturing said wearable device.

29. A method in accordance with claim 28, wherein:
said fabrication apparatus comprises milling apparatus to produce a custom form on which said wearable device is formed.

30. A method in accordance with claim 28, wherein:
said fabrication apparatus comprises vacuum apparatus for forming a plastic material.

31. A method in accordance with claim 28 wherein:
said fabrication apparatus comprises trimming apparatus.

32. A method in accordance with claim 24, comprising:
automatically selecting a device type for said wearable device in response to said first data.

33. A method in accordance with claim 24, comprising:
automatically selecting a device style for said wearable device.

34. A method in accordance with claim 24, comprising:
automatically selecting device type and a device style for said wearable device from said first data.

35. A method in accordance with claim 24, wherein:
said head is an infant's head; and
said wearable device comprises a cranial remodeling device.

36. A method in accordance with claim 35, wherein:
said cranial remodeling device is a customized cranial remodeling device unique to said infant's head.

37. A method in accordance with claim 36, comprising:
automatically selecting a cranial remodeling device type and style in response to said first data.

38. A method in accordance with claim 37, comprising:
automatically selecting features for said cranial remodeling device.

39. A method in accordance with claim 35, comprising:
automatically selecting trim lines for said cranial remodeling device.

40. A method in accordance with claim 35, comprising:
providing fabrication apparatus responsive to said one or more computers for manufacturing said cranial remodeling device.

41. A method in accordance with claim 40, wherein:
said fabrication apparatus comprises milling apparatus to produce a custom form on which said cranial remodeling device is formed.

42. A method in accordance with claim 41, wherein:
said fabrication apparatus comprises vacuum apparatus for forming a plastic material on said custom form.

43. A method in accordance with claim 42, wherein:
said fabrication apparatus comprises trimming apparatus.

44. A method in accordance with claim 40, comprising:
automatically select a cranial remodeling type for said cranial remodeling device in response to said first data.

45. A method in accordance with claim 40, comprising:
automatically selecting a cranial remodeling style for said cranial remodeling device.

46. A method in accordance with claim 40, comprising:
automatically selecting a cranial remodeling type and style for said cranial remodeling device.

\* \* \* \* \*